(12) United States Patent
van Delft et al.

(10) Patent No.: US 8,859,629 B2
(45) Date of Patent: Oct. 14, 2014

(54) FUSED CYCLOOCTYNE COMPOUNDS AND THEIR USE IN METAL-FREE CLICK REACTIONS

(75) Inventors: Floris Louis van Delft, Nijmegen (NL); Floris Petrus Johannes Theodorus Rutjes, Wijchen (NL); Frederik Jan Dommerholt, Beuningen (NL)

(73) Assignee: Synaffix B.V., Oss (NL)

( * ) Notice: Subject to any disclaimer, the term of this patent is extended or adjusted under 35 U.S.C. 154(b) by 66 days.

(21) Appl. No.: 13/643,546

(22) PCT Filed: Apr. 26, 2011

(86) PCT No.: PCT/NL2011/050280
§ 371 (c)(1),
(2), (4) Date: Feb. 14, 2013

(87) PCT Pub. No.: WO2011/136645
PCT Pub. Date: Nov. 3, 2011

(65) Prior Publication Data
US 2013/0137763 A1    May 30, 2013

Related U.S. Application Data

(60) Provisional application No. 61/328,306, filed on Apr. 27, 2010.

(30) Foreign Application Priority Data

Apr. 27, 2010  (EP) .................................... 10161192

(51) Int. Cl.
| | | |
|---|---|---|
| C07C 33/16 | (2006.01) | |
| C07C 271/10 | (2006.01) | |
| A61K 47/48 | (2006.01) | |
| A61K 49/00 | (2006.01) | |
| G01N 33/531 | (2006.01) | |
| G01N 33/68 | (2006.01) | |
| G01N 33/58 | (2006.01) | |
| C07C 271/12 | (2006.01) | |
| G01N 33/532 | (2006.01) | |
| C07C 67/347 | (2006.01) | |
| C07C 29/147 | (2006.01) | |
| C07C 29/62 | (2006.01) | |
| C07C 29/58 | (2006.01) | |

(52) U.S. Cl.
CPC .............. *C07C 33/16* (2013.01); *G01N 33/585* (2013.01); *C07C 271/12* (2013.01); *G01N 33/532* (2013.01); *A61K 47/48023* (2013.01);

*C07C 67/347* (2013.01); *A61K 49/0052* (2013.01); *C07C 29/147* (2013.01); *C07C 29/62* (2013.01); *C07C 2102/24* (2013.01); *C07C 29/58* (2013.01)
USPC ........... 514/729; 514/724; 514/738; 514/480; 514/489; 568/819; 568/821

(58) Field of Classification Search
CPC ................. C07C 33/16; C07C 271/06; A61K 47/48023; A61K 49/0052
USPC .......... 514/729, 724, 738, 480, 489; 568/819, 568/821
See application file for complete search history.

(56) References Cited

U.S. PATENT DOCUMENTS

2009/0068738 A1    3/2009    Bertozzi et al.

FOREIGN PATENT DOCUMENTS

| WO | WO-2009/064366 A2 | 5/2009 |
| WO | WO-2009/067663 A1 | 5/2009 |

OTHER PUBLICATIONS

Debets et al.: "Aza-dibenzocyclooctynes for fast and efficient enzyme PEGylation via copper-free (3 2) cycloaddition", Chem. Commun., vol. 46, Nov. 6, 2009, pp. 97-99, XP002599643.
International Search Report for PCT/NL2011/050280—mailed Aug. 11, 2011.
Ning et al.: "Protein Modification by Strain-Promoted Alkyne-Nitrone Cycloaddition", Angew. Chem. Int. Ed., vol. 49, Apr. 12, 2010, pp. 3065-3068, XP002599644.
Jewett et al., "Rapid Cu-Free Click Chemistry with Readily Synthesized Biarylazacyclooctynones," J. Am. Chem. Soc., 2010 vol. 132, pp. 3688-3690.
Mckay et al., "Nitrones as dipoles for rapid strain-promoted 1,3-dipolar cycloadditions with cyclooctynes," Chem. Commun., vol. 46, 2010, pp. 9331-933.

*Primary Examiner* — Sreeni Padmanabhan
*Assistant Examiner* — Irina Neagu
(74) *Attorney, Agent, or Firm* — Gilberto M. Villacorta; Sunit Talapatra; Foley & Lardner LLP

(57) ABSTRACT

The invention relates to fused cyclooctyne compounds, and to a method for their preparation. The invention also relates to a conjugate wherein a fused cyclooctyne compound according to the invention is conjugated to a label, and to the use of these conjugates in bioorthogonal labeling, imaging and/or modification, such as for example surface modification, of a target molecule. The invention further relates to a method for the modification of a target molecule, wherein a conjugate according to the invention is reacted with a compound comprising a 1,3-dipole or a 1,3-(hetero)diene.

24 Claims, 6 Drawing Sheets

FUSED CYCLOOCTYNE COMPOUNDS AND THEIR USE IN METAL-FREE CLICK REACTIONS

The instant application is a National Stage entry of International Application No. PCT/NL2011/050280 filed on 26 Apr., 2011, which claims priority from U.S. Provisional Patent Application No. 61/328,306, filed on 27 Apr., 2010, and from European Patent Application No. 10161192.9, filed on 27 Apr., 2010.

FIELD OF THE INVENTION

The invention relates to fused cyclooctyne compounds and to a method for their preparation. The fused cyclooctyne compounds according to the invention may be used in metal-free click reactions. Therefore, the invention further relates to a method for the modification of a target molecule by reaction of a fused cyclooctyne conjugate with a target molecule comprising a 1,3-dipole or a 1,3-(hetero)diene. The invention also relates to the use of cyclooctyne conjugates in bioorthogonal labeling, imaging or modification of a target molecule.

BACKGROUND OF THE INVENTION

A revolutionary development in the rapidly expanding field of "chemical biology" is related to chemistry in living systems. Chemistry in living systems concerns chemical reactions that are mild in nature, yet so rapid and high-yielding that they work at about physiological pH, in water, and in the vicinity of biomolecular functionalities. Such reactions may be grouped under the term "bioorthogonal chemistry". In the field of bioorthogonal chemistry there are two main challenges: first, the development of suitable chemistry, and second, the application thereof in living organisms (in vivo).

In the field of chemistry, an enormous toolbox of chemical reactions is available that may be applied to the construction of complex organic molecules. However, the vast majority of such reactions can only be performed under strictly anhydrous conditions, in other words, in the complete absence of water. Although still a good minority of chemical reactions may be performed in, or in the presence of, water, most of these reactions can still only be applied in vitro because the interference of other compounds present in the living organism with the chemicals involved can not be excluded. At present, only a handful of chemical reactions is fully compatible with other functional groups present in the living organism.

An example of such a reaction is the cycloaddition of cyclic alkynes and azides, one of the reactions known as "click reactions". This reaction has become a versatile tool for bioorthogonal labeling and imaging of biomolecules (such as for example proteins, lipids, glycans and the like), proteomics and materials science. In essence, two separate molecular entities, one charged with an azide, and one charged with a strained cycloalkyne, will spontaneously combine into a single molecule by a reaction called strain-promoted azide-alkyne cycloaddition (SPAAC). The power of SPAAC for bioorthogonal labeling lies in the fact that an isolated cyclic alkyne or azide is fully inert to biological functionalities, such as for example amines, thiols, acids or carbonyls, but in combination undergo rapid and irreversible cycloaddition leading to a stable triazole conjugate. For example, azido-modified proteins, obtained by expression in auxotrophic bacteria, genetic engineering or chemical conversion, can be cleanly labeled with biotin, fluorophores, PEG-chains or other functionalities upon simply stirring the azido-protein with a cyclooctyne conjugate. Moreover, the small size of azide has proven highly useful for application of SPAAC in the imaging of specific biomolecules by means of the chemical reporter strategy.

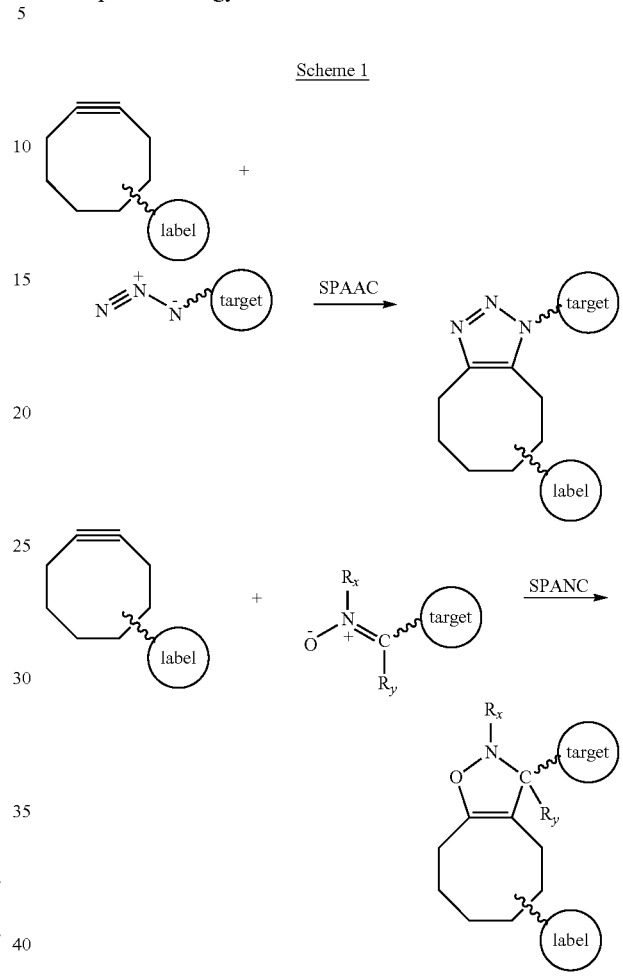

Scheme 1

Apart from azides, cyclooctynes also show high reactivity with other dipoles, such as nitrones and nitrile oxides. For example, the strain-promoted alkyne-nitrone cycloaddition (SPANC) was applied for the N-terminal modification of proteins.

SPAAC and SPANC cycloaddition reactions (Scheme 1) proceed spontaneously, hence in the absence of a (metal) catalyst, and these and a select number of additional cycloadditions are also referred to as "metal-free click reactions".

Several cyclic alkynes and their application in bioorthogonal labeling are described in the prior art. US 2009/0068738, incorporated by reference, relates to modified cycloalkyne compounds and their use in modifying biomolecules via a cycloaddition reaction that may be carried out under physiological conditions. The cycloaddition involves reacting a modified cycloalkyne, such as for example difluorinated cyclooctyne compounds DIFO, DIFO2 and DIFO3, with an azide moiety on a target biomolecule, generating a covalently modified biomolecule. It was observed that fluoride substitution has an accelerating effect on the cycloaddition with azide. For example DIFO3 displays a significantly improved reaction rate constant of up to $k=76 \times 10^{-3}$ $M^{-1}$ $s^{-1}$, versus a maximum of $2.4 \times 10^{-3}$ $M^{-1}$ $s^{-1}$ for non-fluorinated systems.

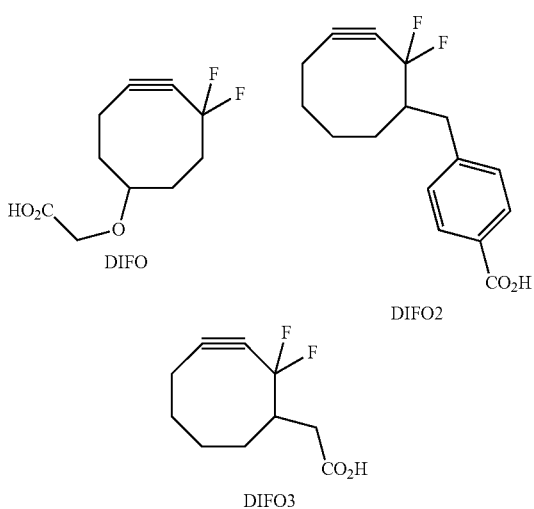

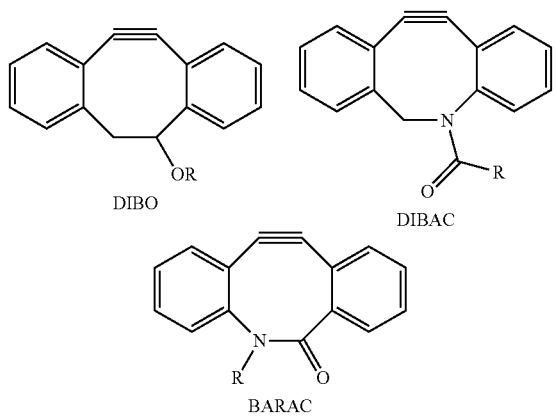

Cyclooctynes wherein the cyclooctyne is fused to aryl groups (benzannulated systems) are disclosed in WO 2009/067663, incorporated by reference, and the reaction kinetics of these dibenzocyclooctyne compounds DIBO in the cycloaddition with azides are further improved ($k=0.12 M^{-1} s^{-1}$).

Azadibenzocyclooctyne DIBAC was developed by van Delft et al. (*Chem. Commun.* 2010, 46, 97-99), incorporated by reference, and shows further improved reaction kinetics in the cycloaddition with azides ($k=0.31 M^{-1} s^{-1}$).

Recently another benzannulated system, biarylazacyclooctynone BARAC, was reported by Bertozzi et al. (*J. Am. Chem. Soc.* 2010, 132, 3688-3690), incorporated by reference. By placing the amide functionality in the ring, the reaction kinetics of the cycloaddition of BARAC with azides was improved significantly ($k=0.96 M^{-1} s^{-1}$).

DIBO and DIBAC were also found to undergo rapid cycloaddition with nitrones as described by Pezacki (*Chem. Commim.* 2010, 46, 931-933) and by van Delft (*Angew. Chem. Int. Ed.* 2010, 49, 3065-3068), both incorporated by reference, with reaction rate constants up to 300 times higher than with azides.

However, the cyclooctyne probes for bioorthogonal labeling known in the prior art suffer from several disadvantages. First of all, widespread application is hampered by the fact that only DIBAC is commercially available. Synthetic preparation requires advanced chemical expertise. In addition, synthesis of the currently available probes is lengthy (eight chemical steps for DIFO2, ten steps for DIFO3, nine steps for DIBAC), and/or low-yielding (10% overall for DIBO). Thirdly, the presence of the two benzannulated aryl moieties in DIBO and DIBAC inflicts both serious steric repulsion as well as lipophilic character. The lipophilic character of DIBO and DIBAC may lead to a specific protein binding by van der Waals interactions, which is undesirable.

Hence, there exists a clear demand for novel, readily accessible and reactive bioorthogonal probes for use in metal-free click reactions, such as 1,3-dipolar cycloaddition with azides, nitrones and other 1,3-dipoles.

SUMMARY OF THE INVENTION

In a first aspect, the present invention relates to a compound of the Formula (Ia), (Ib) or (Ic),

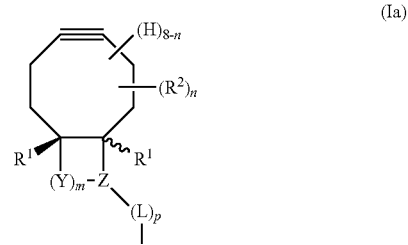
(Ia)

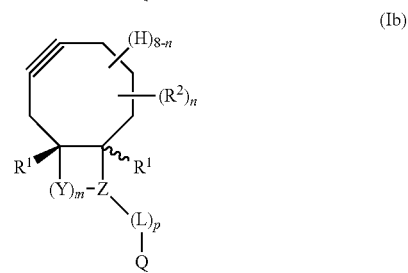
(Ib)

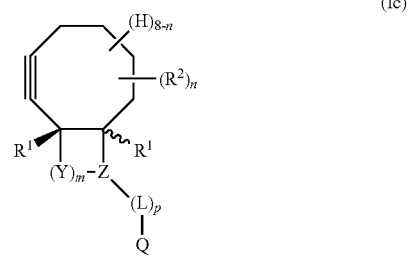
(Ic)

wherein:
m is 0 or 1;
n is 0 to 8;
p is 0 or 1;
Z is N or C($R^3$), wherein $R^3$ is selected from the group consisting of [$(L)_p$-Q], hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)aryl alkyl groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S, wherein the silyl groups are represented by the formula $(R^4)_3Si—$, wherein $R^4$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero atoms selected from the group consisting of O, N and S;

Y is O, C(O) or $C(R^5)_2$, wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups, and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are optionally substituted;

optionally, when m=1, Y and Z together with the bond connecting Y and Z, form a cyclic alkyl group or a (hetero)aryl group, wherein the cyclic alkyl group and the (hetero)aryl group are optionally substituted, provided that when Y and Z form a (hetero)aryl group, then the group $-(L)_p$-Q is a substituent on the (hetero)aryl group;

L is a linking group selected from linear or branched $C_1$-$C_{24}$ alkylene groups, $C_2$-$C_{24}$ alkenylene groups, $C_2$-$C_{24}$ alkynylene groups, $C_3$-$C_{24}$ cycloalkylene groups, $C_5$-$C_{24}$ cycloalkenylene groups, $C_8$-$C_{24}$ cycloalkynylene groups, $C_7$-$C_{24}$ alkyl(hetero)arylene groups, $C_7$-$C_{24}$ (hetero)arylalkylene groups, $C_8$-$C_{24}$ (hetero)arylalkenylene groups, $C_9$-$C_{24}$ (hetero)arylalkynylene groups, the alkylene groups, alkenylene groups, alkynylene groups, cycloalkylene groups, cycloalkenylene groups, cycloalkynylene groups, alkyl (hetero)arylene groups, (hetero)arylalkylene groups, (hetero)arylalkenylene groups and (hetero)arylalkynylene groups optionally being substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^4)_3Si—$, wherein $R^4$ is defined as above;

Q is a functional group selected from the group consisting of hydrogen, halogen, $R^6$, $—CH=C(R^6)_2$, $—C\equiv CR^6$, $—[C(R^6)_2C(R^6)_2O]q—R^6$, wherein q is in the range of 1 to 200, —CN, $—N_3$, —NCX, —XCN, $—XR^6$, $—^+N(R^6)_2$, $—N(R^6)_3$, $—C(X)N(R^6)_2$, $—C(R^6)_2XR^6$, $—C(X)R^6$, $—C(X)XR^6$, $—S(O)R^6$, $—S(O)_2R^6$, $—S(O)OR^6$, $—S(O)_2OR^6$, $—S(O)N(R^6)_2$, $—S(O)_2N(R^6)_2$, $—OS(O)R^6$, $—OS(O)_2R^6$, $—OS(O)OR^6$, $—OS(O)_2OR^6$, $—P(O)(R^6)(OR^6)$, $—P(O)(OR^6)_2$, $—OP(O)(OR^6)_2$, $—Si(R^6)_3$, $—XC(X)R^6$, $—XC(X)XR^6$, $—XC(X)N(R^6)_2$, $—N(R^6)C(X)R^6$, $—N(R^6)C(X)XR^6$ and $—N(R^6)C(X)N(R^6)_2$, wherein X is oxygen or sulphur and wherein $R^6$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups; $R^1$ is independently selected from the group consisting of hydrogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups; and $R^2$ is independently selected from the group consisting of halogen, $—OR^6$, $—NO_2$, —CN, $—S(O)_2R^6$, $C_1$-$C_{12}$ alkyl groups, $C_1$-$C_{12}$ aryl groups, $C_1$-$C_{12}$ alkylaryl groups and $C_1$-$C_{12}$ arylalkyl groups, wherein $R^6$ is as defined above, and wherein the alkyl groups, aryl groups, alkylaryl groups and arylalkyl groups are optionally substituted.

The present invention further relates to a conjugate, such as a cyclooctyne conjugate, wherein a compound of the Formula (Ia), (Ib) and/or (Ic) is conjugated to a label via a functional group Q.

Another aspect of the present invention is to provide a method for preparing a compound of the general Formula (Ia), (Ib) or (Ic), the method comprising the steps of:

(a) Introduction of a fused 3- or 4-membered ring to a cyclooctadiene of the Formula (VIIa), (VIIb) or (VIIc):

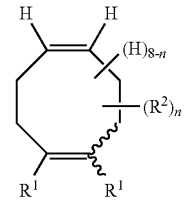

(VIIa)

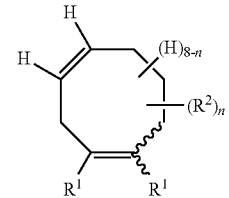

(VIIb)

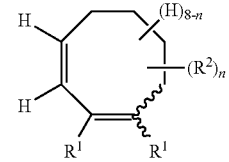

(VIIc)

wherein:

n=0 to 8;

$R^1$ is independently selected from the group consisting of hydrogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups; and $R^2$ is independently selected from the group consisting of halogen, $—OR^6$, $—NO_2$, —CN, $—S(O)_2R^6$, $C_1$-$C_{12}$ alkyl groups, $C_1$-$C_{12}$ aryl groups, $C_1$-$C_{12}$ alkylaryl groups and $C_1$-$C_{12}$ arylalkyl groups, wherein the alkyl groups, aryl groups, alkylaryl groups and arylalkyl groups are optionally substituted, and wherein $R^6$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, to form a bicyclic cyclooctene compound,
(b) Bromination of the obtained bicyclic cyclooctene compound to form a bicyclic cyclooctane compound, and
(c) Dehydrobromination of the obtained bicyclic cyclooctane compound.

The present invention also relates to a method for the modification of a target molecule, wherein a conjugate according to the invention is reacted with a compound comprising a 1,3-dipole or a 1,3-(hetero)diene.

Yet another aspect of the present invention is the use of a conjugate according to the invention for bioorthogonal labeling, imaging or modification, such as for example surface modification, of a target molecule.

Finally, the invention relates to a composition comprising a conjugate according to the invention, further comprising a pharmaceutically acceptable carrier.

DETAILED DESCRIPTION OF THE INVENTION

Definitions

Figure 1:
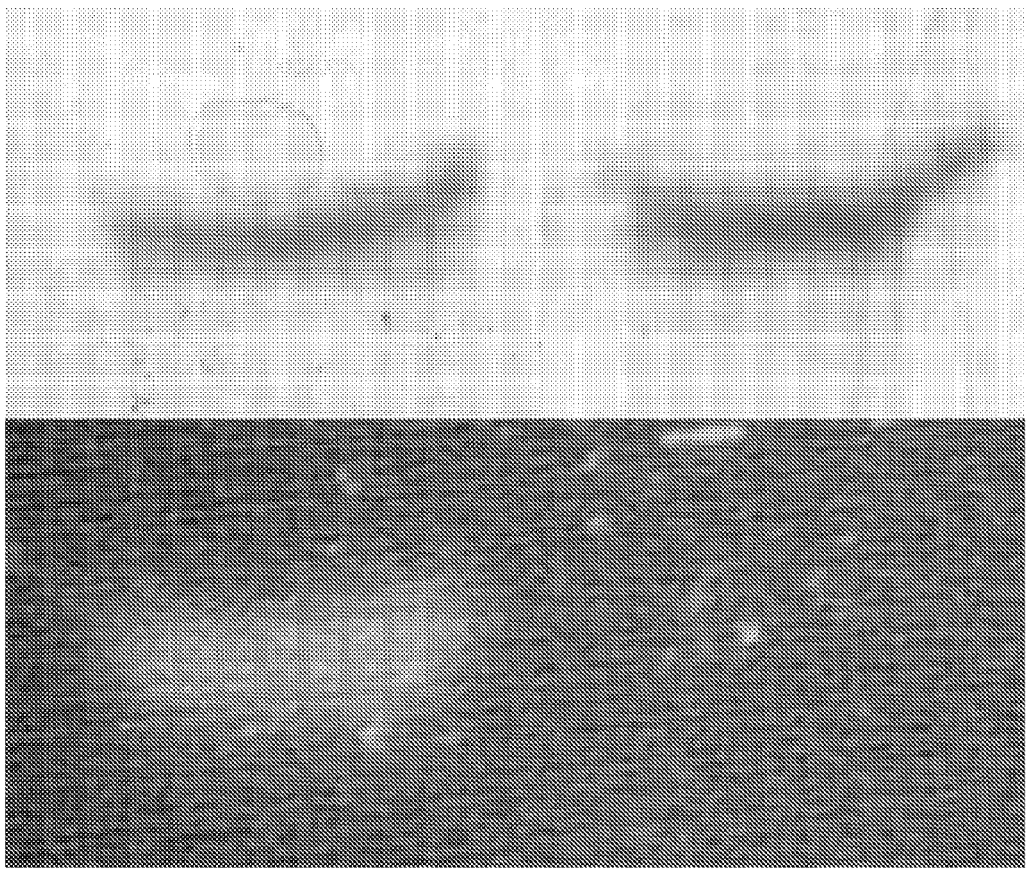
FIG. 1 depicts the SDS-PAGE analyses of the SPAAC reaction of azide-labeled capsid protein with a cyclooctyne conjugated to Alexa Fluor 555 (left) and of the blank reaction (right).

The verb "to comprise" as is used in this description and in the claims and its conjugations is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The compounds disclosed in this description and in the claims may be described as fused cyclooctyne compounds, i.e. cyclooctyne compounds wherein a second ring structure is fused to the cyclooctyne moiety. The triple bond of the cyclooctyne moiety in a fused cyclooctyne compound may be located on either one of the three possible locations, i.e. on the 2, 3 or 4 position of the cyclooctyne moiety (numbering according to "IUPAC Nomenclature of Organic Chemistry", Rule A31.2). The description of any fused cyclooctyne compound in this description and in the claims is meant to include all three individual regioisomers of the cyclooctyne moiety.

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise.

The compounds disclosed in this description and in the claims may further exist as exo and endo regioisomers. Unless stated otherwise, the description of any compound in the description and in the claims is meant to include both the individual exo and the individual endo regioisomer of a compound, as well as mixtures thereof.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application.

Unsubstituted alkyl groups have the general formula $C_nH_{2n+1}$ and may be linear or branched. Unsubstituted alkyl groups may also contain a cyclic moiety, and thus have the concomitant general formula $C_nH_{2n-1}$. Optionally, the alkyl groups are substituted by one or more substituents further specified in this document. Examples of suitable alkyl groups include, but are not limited to, methyl, ethyl, propyl, 2-propyl, t-butyl, 1-hexyl. 1-dodecyl and the like.

Unsubstituted alkenyl groups have the general formula $C_nH_{2n-1}$, and may be linear or branched. Examples of suitable alkenyl groups include, but are not limited to, ethenyl, propenyl, isopropenyl, butenyl, pentenyl, decenyl, octadecenyl, and eicosenyl and the like. Unsubstituted alkenyl groups may also contain a cyclic moiety, and thus have the concomitant general formula $C_nH_{2n-3}$.

Unsubstituted alkenes have the general formula $C_nH_{2n}$ whereas unsubstituted alkynes have the general formula $C_nH_{2n-2}$.

Aryl groups comprise at least six carbon atoms and may include monocyclic, bicyclic and polycyclic structures. Optionally, the aryl groups may be substituted by one or more substituents further specified in this document. Examples of aryl groups include groups such as for example phenyl, naphthyl, anthracyl and the like.

Arylalkyl groups and alkylaryl groups comprise at least seven carbon atoms and may include monocyclic and bicyclic structures. Optionally, the aryl groups may be substituted by one or more substituents further specified in this document. An arylalkyl group is for example benzyl and the like. An alkylaryl group is for example 4-t-butylphenyl and the like.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group.

A heteroaryl group comprises one to four heteroatoms selected from the group consisting of oxygen, nitrogen and sulphur.

Fused Cyclooctyne Compounds

Based on the fact that the reactivity of cycloalkynes increases with decreasing ring size, conjugates of cycloalkynes with less than eight carbon atoms would be of high interest for application in bioorthogonal chemistry. Unfortunately, to date cycloheptyne and smaller rings cannot be isolated in pure form, due to increasing strain energy as a result of deviation from the ideal 180° C—C≡C angle.

An alternative way to increase strain energy is by benzannulation of cyclooctyne to aryl groups, the strategy followed in WO 2009/067663 for DIBO. The strain energy may then be further enhanced by introduction of another sp²-type atom in the ring, the approach followed by van Delft for DIBAC and by Bertozzi for BARAC. However, as was mentioned above, the presence of two aryl moieties in cyclooctyne not only gives rise to serious steric repulsion, but also increases the lipophilic character of the cyclooctyne compounds, which is undesired.

The present inventors found that a very efficient way to induce additional ring strain involves fusion of a cyclooctyne to a 3- or 4-membered ring, leading to fused cyclooctyne compounds, more in particular to bicyclo[6.1.0]nonyne and bicyclo[6.2.0]decyne systems, respectively. These bicyclic systems are surprisingly well suited as bioorthogonal probes, since they combine relative stability with a high reactivity in (3+2) cycloadditions with 1,3-dipoles and in (hetero) Diels-Alder reactions with 1,3-(hetero)dienes. Furthermore, the fused 3- or 4-membered ring structure, apart from inflicting ring strain, is also perfectly suitable for the positioning of a handle for the conjugation to functional groups and/or labels and can be conveniently functionalized for applications such as bioorthogonal labeling, imaging and/or modification, such as for example surface modification, of target molecules.

In a first aspect, the present invention therefore relates to compounds of the general Formula (Ia), (Ib) or (Ic),

(Ia)

(Ib)

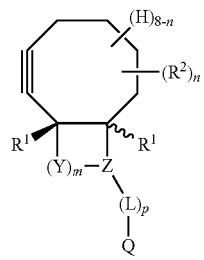
(Ic)

wherein:
m is 0 or 1;
n is 0 to 8;
p is 0 or 1;
Z is N or $C(R^3)$, wherein $R^3$ is selected from the group consisting of $[(L)_p$-Q], hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S, wherein the silyl groups are represented by the formula $(R^4)_3Si$—, wherein $R^4$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups. $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S;
Y is O, C(O) or $C(R^5)_2$, wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups, and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are optionally substituted;
optionally, when m=1, Y and Z together with the bond connecting Y and Z, form a cyclic alkyl group or a (hetero)aryl group, wherein the cyclic alkyl group and the (hetero)aryl group are optionally substituted, provided that when Y and Z form a (hetero)aryl group, then the group -(L)$_p$-Q is a substituent on the (hetero)aryl group;

L is a linking group selected from linear or branched $C_1$-$C_{24}$ alkylene groups, $C_2$-$C_{24}$ alkenylene groups, $C_2$-$C_{24}$ alkynylene groups, $C_3$-$C_{24}$ cycloalkylene groups, $C_5$-$C_{24}$ cycloalkenylene groups, $C_8$-$C_{24}$ cycloalkynylene groups, $C_7$-$C_{24}$ alkyl(hetero)arylene groups, $C_7$-$C_{24}$ (hetero)arylalkylene groups, $C_8$-$C_{24}$ (hetero)arylalkenylene groups, $C_9$-$C_{24}$ (hetero)arylalkynylene groups, the alkylene groups, alkenylene groups, alkynylene groups, cycloalkylene groups, cycloalkenylene groups, cycloalkynylene groups, alkyl(hetero)arylene groups, (hetero)arylalkylene groups, (hetero)arylalkenylene groups and (hetero)arylalkynylene groups optionally being substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^4)_3Si-$, wherein $R^4$ is defined as above;

Q is a functional group selected from the group consisting of hydrogen, halogen, $R^6$, $-CH=C(R^6)_2$, $-C\equiv CR^6$, $-[C(R^6)_2C(R^6)_2O]_q-R^6$, wherein q is in the range of 1 to 200, $-CN$, $-N_3$, $-NCX$, $-XCN$, $-XR^6$, $-N(R^6)_2$, $-^+N(R^6)_3$, $-C(X)N(R^6)_2$, $-C(R^6)_2XR^6$, $-C(X)R^6$, $-C(X)XR^6$, $-S(O)R^6$, $-S(O)_2R^6$, $-S(O)OR^6$, $-S(O)_2OR^6$, $-S(O)N(R^6)_2$, $-S(O)_2N(R^6)_2$, $-OS(O)R^6$, $-OS(O)_2R^6$, $-OS(O)OR^6$, $-OS(O)_2OR^6$, $-P(O)(R^6)(OR^6)$, $-P(O)(OR^6)_2$, $-OP(O)(OR^6)_2$, $-Si(R^6)_3$, $-XC(X)R^6$, $-XC(X)XR^6$, $-XC(X)N(R^6)_2$, $-N(R^6)C(X)R^6$, $-N(R^6)C(X)XR^6$ and $-N(R^6)C(X)N(R^6)_2$, wherein X is oxygen or sulphur and wherein $R^6$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

$R^1$ is independently selected from the group consisting of hydrogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups; and $R^2$ is independently selected from the group consisting of halogen, $-OR^6$, $-NO_2$, $-CN$, $-S(O)_2R^6$, $C_1$-$C_{12}$ alkyl groups, $C_1$-$C_{12}$ aryl groups, $C_1$-$C_{12}$ alkylaryl groups and $C_1$-$C_{12}$ arylalkyl groups, wherein $R^6$ is as defined above, and wherein the alkyl groups, aryl groups, alkylaryl groups and arylalkyl groups are optionally substituted.

An advantage of the fused cyclooctyne compounds according to the present invention is that they are easily synthesized. A further advantage is that they are amenable to simple and straightforward modification of the various parts of the molecule.

The fused cyclooctyne compound of Formula (Ia) is preferred. In this compound, the triple bond is located on the 4-position of the cyclooctyne moiety, i.e. opposite to the fused 3- or 4-membered ring. This may result in a decreased number of potential regioisomers possible for (Ia), depending on the nature of the substituents on the cyclooctyne compound.

In the compounds of Formula (Ia), (Ib) and (Ic), the -[(L)$_p$-Q] substituent on Z may be positioned on the exo or on the endo position respective to the cyclooctyne ring. The two $R^1$-substitutents may be in a cis or in a trans position relative to each other.

Preferably, Q is selected from the group consisting of $-CN$, $-N_3$, $-NCX$, $-XCN$, $-XR^6$, $-N(R^6)_2$, $-^+N(R^6)_3$, $-C(X)N(R^6)_2$, $-C(R^6)_2XR^6$, $-C(X)R^6$, $-C(X)XR^6$, $-XC(X)R^6$, $-XC(X)XR^6$, $-XC(X)N(R^6)_2$, $-N(R^6)C(X)R^6$, $-N(R^6)C(X)XR^6$ and $-N(R^6)C(X)N(R^6)_2$, wherein X and $R^6$ are as defined above. More preferably, X is oxygen. Most preferably, Q is selected from the group consisting of $-OR^6$, $-N(R^6)_2$, $-^+N(R^6)_3$, $-C(O)N(R^6)_2$, $-C(O)OR^6$, $-OC(O)R^6$, $-OC(O)OR^6$, $-OC(O)N(R^6)_2$, $-N(R^6)C(O)R^6$, $-N(R^6)C(O)OR^6$ and $-N(R^6)C(O)N(R^6)_2$. Furthermore, the functional group Q may optionally be masked or protected. The $R^6$ groups may be selected independently from each other, which means that the two $R^6$ groups present in, for example, a $-N(R^6)_2$ substituent may be different from each other.

In one embodiment, p is 0, i.e. Q is bonded directly to Z. In another embodiment, p is 1. In yet another embodiment, p is 1 and L is $CH_2$.

In a preferred embodiment, $R_1$ is hydrogen.

In another preferred embodiment, n is 0. In yet another preferred embodiment, $R^2$ is an electron-withdrawing group, i.e. a group with a positive value for the Hammett substituent constant σ. Suitable electron-withdrawing groups are known to a person skilled in the art, and include for example halogen (in particular F), $-OR^6$, $-NO_2$, $-CN$, $-S(O)_2R^6$, substituted $C_1$-$C_{12}$ alkyl groups, substituted $C_1$-$C_{12}$ aryl groups or substituted $C_1$-$C_{12}$ alkylaryl groups, wherein the substituents are electron-withdrawing groups. Preferably, the substituted alkyl groups, aryl groups and alkylaryl groups are fluorinated $C_1$-$C_{12}$ alkyl groups (such as for example $-CF_3$), fluorinated $C_1$-$C_{12}$ aryl groups (such as for example $-C_6F_5$) or fluorinated $C_1$-$C_{12}$ alkylaryl groups (such as for example $-[3,5-(CF_3)_2(C_6H_3)]$).

Compounds with m=0 and Z=CR$^3$

A specific class of compounds the present invention relates to is the class of compounds according to Formula (Ia), (Ib) or (Ic) wherein the cyclooctyne moiety is fused to a three-membered ring structure. Therefore, in a preferred embodiment of the present invention m, as defined above, is 0.

In a further preferred embodiment, Z is C(R$^3$), wherein $R^3$ is as defined above. The present invention therefore also relates to a compound according to Formula (Ia), (Ib) or (Ic), wherein the compound is of the Formula (IIa), (IIb) or (IIc):

(IIa)

(IIb)

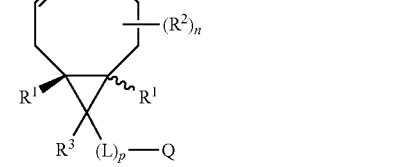

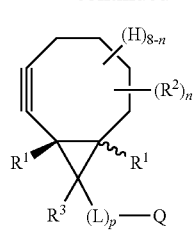

(IIc)

wherein n, p, $R^1$, $R^2$, $R^3$, L and Q are as defined above for compounds of the Formula (Ia), (Ib) and (Ic).

As was already mentioned above, the -[(L)$_p$-Q] substituent in the compounds of Formula (IIa), (IIb) and (IIc), may be positioned exo or endo with respect to the cyclooctyne ring, and the two $R^1$ substituents may be positioned in a cis or in a trans position relative to each other. In a preferred embodiment, the $R^1$ substituents are in a cis position.

In one embodiment, p is 0, i.e. Q is bonded directly to the cyclopropyl ring. In another embodiment, p is 1. In yet another embodiment, p is 1 and L is $CH_2$.

Also in compounds of the Formula (IIa), (IIb) or (IIc), both when p is 0 and when p is 1, Q is preferably selected from the group consisting of —CN, —$N_3$, —NCX, —XCN, —$XR^6$, —$N(R^6)_2$, —$^+N(R^6)_3$, —$C(X)N(R^6)_2$, —$C(R^6)_2XR^6$, —$C(X)R^6$, —$C(X)XR^6$, —$XC(X)R^6$, —$XC(X)XR^6$, —$XC(X)N(R^6)_2$, —$N(R^6)C(X)R^6$, —$N(R^6)C(X)XR^6$ and —$N(R^6)C(X)N(R^6)_2$, wherein X and $R^6$ are as defined above. More preferably, X is oxygen. Most preferably, Q is selected from the group consisting of —$OR^6$, —$N(R^6)_2$, —$^+N(R^6)_3$, —$C(O)N(R^6)_2$, —$C(O)OR^6$, —$OC(O)R^6$, —$OC(O)OR^6$, —$OC(O)N(R^6)_2$, —$N(R^6)C(O)R^6$, —$N(R^6)C(O)OR^6$ and —$N(R^6)C(O)N(R^6)_2$. Furthermore, the functional group Q may optionally be masked or protected. The $R^6$ groups may be selected independently from each other, which means that the two $R^6$ groups present in, for example, a —$N(R^6)_2$ substituent may be different from each other. In a preferred embodiment, Q is —$OR^6$, preferably —OH. In another preferred embodiment. Q is —$C(O)OR^6$.

In another preferred embodiment, $R^3$ is hydrogen or [(L)$_p$-Q].

In a preferred embodiment, $R^1$ is hydrogen.

In another preferred embodiment, n is 0. In yet another preferred embodiment, $R^2$ is an electron-withdrawing group, i.e. a group with a positive value for the Hammett substituent constant σ. Suitable electron-withdrawing groups are known to a person skilled in the art, and include for example halogen (in particular F), —$OR^6$, —$NO_2$, —CN, —$S(O)_2R^6$, substituted $C_1$-$C_{12}$ alkyl groups, substituted $C_1$-$C_{12}$ aryl groups or substituted $C_1$-$C_{12}$ alkylaryl groups, wherein the substituents are electron-withdrawing groups. Preferably, the substituted alkyl groups, aryl groups and alkylaryl groups are fluorinated $C_1$-$C_{12}$ alkyl groups (such as for example —$CF_3$), fluorinated $C_1$-$C_{12}$ aryl groups (such as for example —$C_6F_5$) or fluorinated $C_1$-$C_{12}$ alkylaryl groups (such as for example -[3,5-$(CF_3)_2(C_6H_3)$]).

Of the compounds of Formula (IIa), (IIb) and (IIc), compounds of the Formula (IIa) are preferred since they may possess an axis or a plane of symmetry, thus reducing the number of potential regioisomers that may be formed.

An embodiment wherein p is 1. L is $CH_2$, Q is —OH, $R^1$ is hydrogen, $R^3$ is hydrogen or [(L)$_p$-Q] and n is 0 is particularly preferred.

Compounds with m=0 and Z=N

The present invention also relates to compounds of the general Formula (Ia), (Ib) or (Ic), wherein m is 0 and Z is N. These compounds have the general Formula (IIIa), (IIIb) or (IIIc):

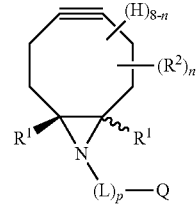

(IIIa)

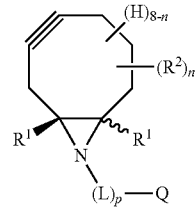

(IIIb)

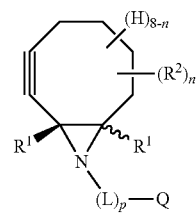

(IIIc)

wherein n, p, $R^1$, $R^2$, L and Q are as defined above for compounds of the Formula (Ia), (Ib) and (Ic).

The two $R^1$ substituents may be positioned in a cis or in a trans position relative to each other. In a preferred embodiment, the $R^1$ substituents are in a cis position.

In one embodiment, p is 0, i.e. Q is bonded directly to N. In another embodiment, p is 1. In yet another embodiment, p is 1 and L is $CH_2$.

Also in compounds of the Formula (IIIa), (IIIb) or (IIIc), both when p is 0 and when p is 1, Q is preferably selected from the group consisting of —CN, —$N_3$, —NCX, —XCN, —$XR^6$, —$N(R^6)_2$, —$^+N(R^6)_3$, —$C(X)N(R^6)_2$, —$C(R^6)_2XR^6$, —$C(X)R^6$, —$C(X)XR^6$, —$XC(X)R^6$, —$XC(X)XR^6$, —$XC(X)N(R^6)_2$, —$N(R^6)C(X)R^6$, —$N(R^6)C(X)XR^6$ and —$N(R^6)C(X)N(R^6)_2$, wherein X and $R^6$ are as defined above. More preferably, X is oxygen. Most preferably, Q is selected from the group consisting of —$OR^6$, —$N(R^6)_2$, —$^+N(R^6)_3$, —$C(O)N(R^6)_2$, —$C(O)OR^6$, —$OC(O)R^6$, —$OC(O)OR^6$, —$OC(O)N(R^6)_2$, —$N(R^6)C(O)R^6$, —$N(R^6)C(O)OR^6$ and —$N(R^6)C(O)N(R^6)_2$. Furthermore, the functional group Q may optionally be masked or protected. The $R^6$ groups may be selected independently from each other, which means that the two $R^6$ groups present in, for example, a —$N(R^6)_2$ substituent may be different from each other.

In a preferred embodiment, $R^1$ is hydrogen.

In another preferred embodiment, n is 0. In yet another preferred embodiment, $R^2$ is an electron-withdrawing group, i.e. a group with a positive value for the Hammett substituent constant σ. Suitable electron-withdrawing groups are known to a person skilled in the art, and include for example halogen (in particular F), —OR$^6$, —NO$_2$, —CN, —S(O)$_2$R$^6$, substituted C$_1$-C$_{12}$ alkyl groups, substituted C$_1$-C$_{12}$ aryl groups or substituted C$_1$-C$_{12}$ alkylaryl groups, wherein the substituents are electron-withdrawing groups. Preferably, the substituted alkyl groups, aryl groups and alkylaryl groups are fluorinated C$_1$-C$_{12}$ alkyl groups (such as for example —CF$_3$), fluorinated C$_1$-C$_{12}$ aryl groups (such as for example —C$_6$F$_5$) or fluorinated C$_1$-C$_{12}$ alkylaryl groups (such as for example –[3,5-(CF$_3$)$_2$(C$_6$H$_3$)]).

Of the compounds of Formula (IIIa). (IIIb) and (IIIc), compounds of the Formula (IIIa) are preferred since they possess an element of symmetry, thus reducing the number of potential regioisomers that may be formed.

Compounds with m=1 and Z=C(R$^3$)

Furthermore, the present invention relates to compounds of the general Formula (Ia), (Ib) or (Ic) wherein m is 1 and Z is C(R$^3$), and these compounds have the general Formula (IVa), (IVb) or (IVc):

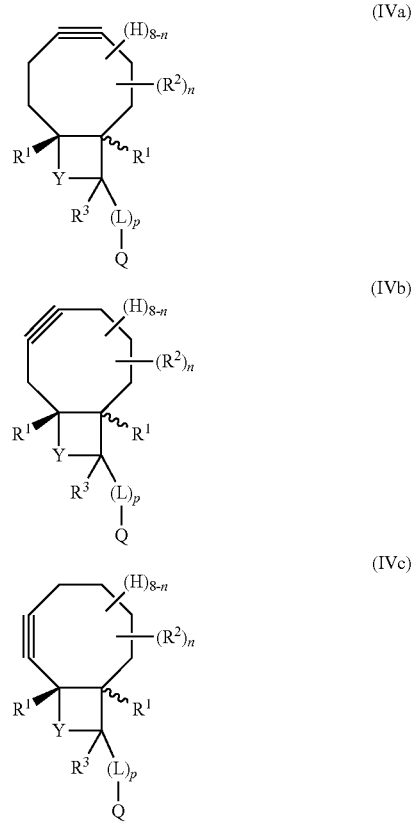

wherein Y is O, C(O) or C(R$^5$)$_2$, and n, p, L, Q, R$^1$, R$^2$, R$^3$ and R$^5$ are as defined above.

Also in the compounds of Formula (IVa), (IVb) and (IVc), the -[(L)$_p$-Q] substituent may be positioned exo or endo with respect to the cyclooctyne ring, and the two R$^1$ substituents may be positioned in a cis or in a trans position relative to each other.

In the compounds of Formula (IVa), (IVb) and (IVc) as depicted above, the Z-group, i.e. the C-atom bonded to R$^3$ and to the -[(L)$_p$-Q] substituent, is located at the 9-position of the fused cyclooctyne compound. However, the regioisomers of (IVb) and (IVc) wherein this Z-group is positioned on the 10-position of the fused bicyclodecyne compound are also included, whereby the -[(L)$_p$-Q] substituent may be positioned on the exo or the endo position.

In one embodiment, p is 0, i.e. Q is bonded directly to the cyclobutyl ring. In another embodiment, p is 1. In yet another embodiment, p is 1 and L is CH$_2$.

Also in compounds of the Formula (IVa), (IVb) or (IVc), both when p is 0 and when p is 1, Q is preferably selected from the group consisting of —CN, —N$_3$, —NCX, —XCN, —XR$^6$, —N(R$^6$)$_2$, —$^+$N(R$^6$)$_3$, —C(X)N(R$^6$)$_2$, —C(R$^6$)$_2$XR$^6$, —C(X)R$^6$, —C(X)XR$^6$, —XC(X)R$^6$, —XC(X)XR$^6$, —XC(X)N(R$^6$)$_2$, —N(R$^6$)C(X)R$^6$, —N(R$^6$)C(X)XR$^6$ and —N(R$^6$)C(X)N(R$^6$)$_2$, wherein X and R$^6$ are as defined above. More preferably, X is oxygen. Most preferably, Q is selected from the group consisting of —OR$^6$, —N(R$^6$)$_2$, —$^+$N(R$^6$)$_3$, —C(O)N(R$^6$)$_2$, —C(O)OR$^6$, —OC(O)R$^6$, —OC(O)OR$^6$, —OC(O)N(R$^6$)$_2$, —N(R$^6$)C(O)R$^6$, —N(R$^6$)C(O)OR$^6$ and —N(R$^6$)C(O)N(R$^6$)$_2$. Furthermore, the functional group Q may optionally be masked or protected. The R$^6$ groups may be selected independently from each other, which means that the two R$^6$ groups present in, for example, a —N(R$^6$)$_2$ substituent may be different from each other.

In a preferred embodiment, Y is O. In another preferred embodiment, Y is C(O). Both when Y is O and when Y is C(O), it is preferred that R$^1$ is hydrogen.

In another preferred embodiment, n is 0. In yet another preferred embodiment, R$^2$ is an electron-withdrawing group, i.e. a group with a positive value for the Hammett substituent constant σ. Suitable electron-withdrawing groups are known to a person skilled in the art, and include for example halogen (in particular F), —OR$^6$, —NO$_2$, —CN, —S(O)$_2$R$^6$, substituted C$_1$-C$_{12}$ alkyl groups, substituted C$_1$-C$_{12}$ aryl groups or substituted C$_1$-C$_{12}$ alkylaryl groups, wherein the substituents are electron-withdrawing groups. Preferably, the substituted alkyl groups, aryl groups and alkylaryl groups are fluorinated C$_1$-C$_{12}$ alkyl groups (such as for example —CF$_3$), fluorinated C$_1$-C$_{12}$ aryl groups (such as for example —C$_6$F$_5$) or fluorinated C$_1$-C$_{12}$ alkylaryl groups (such as for example –[3,5-(CF$_3$)$_2$(C$_5$H$_3$)]).

The compound of Formula (IVa) is preferred. In this compound, the triple bond is located on the 4-position of the cyclooctyne moiety, i.e. opposite to the fused cyclobutyl ring.

Compounds with m=1 and Z=N

The present invention also relates to compounds of the general Formula (Ia), (Ib) or (Ic) wherein m is 1 and Z is N. These compounds have the general Formula (Va), (Vb) or (Vc):

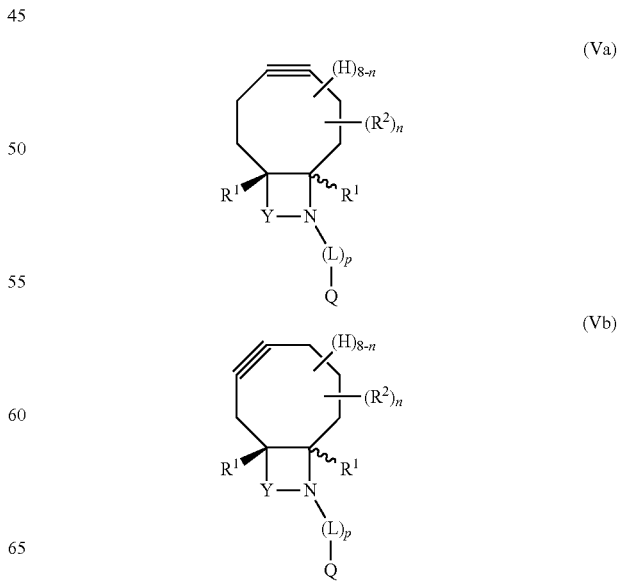

-continued

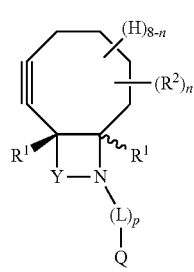
(Vc)

wherein Y is C(O) or C($R^5$)$_2$, and n, p, L, Q, $R^1$, $R^2$ and $R^5$ are as defined above.

In the compounds according to Formula (Va), (Vb) or (Vc) as shown here, the N-atom of the 4-membered ring is positioned on the 9-position of the bicyclic system. However, the present invention also relates to the regioisomers of Formula (Vb) or (Vc) wherein the N-atom of the 4-membered ring is positioned on the 10-position of the bicyclic system. In addition, the two $R^1$-substituents may be positioned cis or trans with respect to each other.

In one embodiment, p is 0, i.e. Q is bonded directly to the 4-membered ring. In another embodiment, p is 1. In yet another embodiment, p is 1 and L is $CH_2$.

Also in compounds of the Formula (Va), (Vb) or (Vc), both when p is 0 and when p is 1, Q is preferably selected from the group consisting of —CN, —$N_3$, —NCX, —XCN, —$XR^6$, —N($R^6$)$_2$, —$^+$N($R^6$)$_3$, —C(X)N($R^6$)$_2$, —C($R^6$)$_2$$XR^6$, —C(X)$R^6$, —C(X)$XR^6$, —XC(X)$R^6$, —XC(X)$XR^6$, —XC(X)N($R^6$)$_2$, —N($R^6$)C(X)$R^6$, —N($R^6$)C(X)$XR^6$ and —N($R^6$)C(X)N($R^6$)$_2$, wherein X and $R^6$ are as defined above. More preferably, X is oxygen. Most preferably, Q is selected from the group consisting of —$OR^6$, —N($R^6$)$_2$, —$^+$N($R^6$)$_3$, —C(O)N($R^6$)$_2$, —C(O)$OR^6$, —OC(O)$R^6$, —OC(O)$OR^6$, —OC(O)N($R^6$)$_2$, —N($R^6$)C(O)$R^6$, —N($R^6$)C(O)$OR^6$ and —N($R^6$)C(O)N($R^6$)$_2$. Furthermore, the functional group Q may optionally be masked or protected. The $R^6$ groups may be selected independently from each other, which means that the two $R^6$ groups present in, for example, a —N($R^6$)$_2$ substituent may be different from each other.

If Y is C($R^5$)$_2$, $R^5$ is preferably hydrogen. Both when Y is C($R^5$)$_2$ and when Y is C(O), it is preferred that $R^1$ is hydrogen.

In another preferred embodiment, n is 0. In yet another preferred embodiment, $R^2$ is an electron-withdrawing group, i.e. a group with a positive value for the Hammett substituent constant σ. Suitable electron-withdrawing groups are known to a person skilled in the art, and include for example halogen (in particular F), —$OR^6$, —$NO_2$, —CN, —S(O)$_2$$R^6$, substituted $C_1$-$C_{12}$ alkyl groups, substituted $C_1$-$C_{12}$ aryl groups or substituted $C_1$-$C_{12}$ alkylaryl groups, wherein the substituents are electron-withdrawing groups. Preferably, the substituted alkyl groups, aryl groups and alkylaryl groups are fluorinated $C_1$-$C_{12}$ alkyl groups (such as for example —$CF_3$), fluorinated $C_1$-$C_{12}$ aryl groups (such as for example —$C_6F_5$) or fluorinated $C_1$-$C_{12}$ alkylaryl groups (such as for example -[3,5-($CF_3$)$_2$($C_6H_3$)]).

As explained above, the compound of Formula (Va) wherein the triple bond is located on the 4-position of the cyclooctyne moiety, i.e. opposite to the fused cyclobutyl ring, is preferred.

Compounds with m=1 and Y and Z Form a Cyclic Alkyl or (Hetero)aryl Group

The invention also relates to compounds of general Formula (Ia), (Ib) or (Ic) wherein, when m=1, Y and Z together with the bond connecting Y and Z, form a cyclic alkyl group or a (hetero)aryl group, wherein the cyclic alkyl group and the (hetero)aryl group are optionally substituted, provided that when Y and Z form a (hetero)aryl group, then the group -(L)$_p$-Q is a substituent on the (hetero)aryl group.

It is preferred that the cyclic group is an aryl group, in particular a benzannulated aryl group as in Formula (VIa), (VIb) and (VIc):

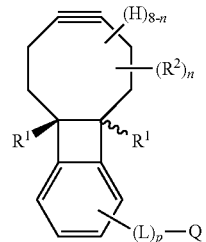
(VIa)

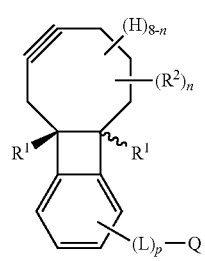
(VIb)

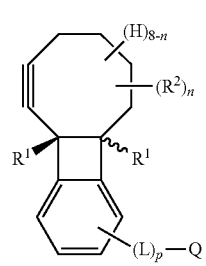
(VIc)

wherein p, n, $R^1$, $R^2$, L and Q are as defined above.

The -(L)$_p$-Q substituent may be located on either the ortho or the meta position of the benzannulated aryl group, and also in compounds of the Formula (VIa), (VIb) and (VIc) the $R^1$-substituents may be positioned cis or trans relative to each other.

In one embodiment, p is 0, i.e. Q is bonded directly to the aryl group. In another embodiment, p is 1. In yet another embodiment, p is 1 and L is $CH_2$.

Q is preferably selected, both for p is 0 as for p is 1, from the group consisting of —CN. —$N_3$, —NCX, —XCN, —$XR^6$, —N($R^6$)$_2$, —C(X)N($R^6$)$_2$, —C($R^6$)$_2$$XR^6$, —C(X)$R^6$, —C(X)$XR^6$, —XC(X)$R^6$, —XC(X)$XR^6$, —XC(X)N($R^6$)$_2$, —N($R^6$)C(X)$R^6$, —N($R^6$)C(X)$XR^6$ and —N($R^6$)C(X)N($R^6$)$_2$, wherein X and $R^6$ are as defined above. More preferably, X is oxygen. Most preferably, Q is selected from the group consisting of —$OR^6$, —N($R^6$)$_2$, —$^+$N($R^6$)$_3$, —C(O)N($R^6$)$_2$, —C(O)$OR^6$, —OC(O)$R^6$, —OC(O)$OR^6$, —OC(O)N($R^6$)$_2$, —N($R^6$)C(O)$R^6$, —N($R^6$)C(O)$OR^6$ and —N($R^6$)C(O)N($R^6$)$_2$. Furthermore, the functional group Q may optionally be masked or protected. The $R^6$ groups may be selected independently from each other, which means that the two $R^6$ groups present in, for example, a —N($R^6$)$_2$ substituent may be different from each other.

In a preferred embodiment, $R^1$ is hydrogen. In another preferred embodiment, n is 0. In yet another preferred embodiment, $R^2$ is an electron-withdrawing group, i.e. a group with a positive value for the Hammett substituent constant σ. Suitable electron-withdrawing groups are known to a person skilled in the art, and include for example halogen (in particular F), —$OR^6$, —$NO_2$, —CN, —$S(O)_2R^6$, substituted $C_1$-$C_{12}$ alkyl groups, substituted $C_1$-$C_{12}$ aryl groups or substituted $C_1$-$C_{12}$ alkylaryl groups, wherein the substituents are electron-withdrawing groups. Preferably, the substituted alkyl groups, aryl groups and alkylaryl groups are fluorinated $C_1$-$C_{12}$ alkyl groups (such as for example —$CF_3$), fluorinated $C_1$-$C_{12}$ aryl groups (such as for example —$C_6F_5$) or fluorinated $C_1$-$C_{12}$ alkylaryl groups (such as for example -[3,5-$(CF_3)_2(C_6H_3)$]).

As explained above, the compound of Formula (VIa) wherein the triple bond is located on the 4-position of the cyclooctyne moiety is preferred.

Conjugates

The fused cyclooctyne compounds according to the present invention are very suitable for use in metal-free click reactions, and consequently these compounds are versatile tools in applications such as for example bioorthogonal labeling, imaging and/or modification, including surface modification, of a large range of target molecules. It is an aspect of the present invention to provide a conjugate wherein a compound of the Formula (Ia), (Ib) and/or (Ic) according to the invention is conjugated to a label via a functional group Q.

The term "label" refers to any identifying tag that may be conjugated to a compound of the Formula (Ia), (Ib) and (Ic) according to the invention. A wide variety of labels are known in the art, for a wide variety of different applications. Depending on the specific application, a suitable label for that specific application may be selected. Suitable labels for specific applications are known to the person skilled in the art, and include, but are not limited to, all kinds of fluorophores, biotin, polyethylene glycol (PEG) chains, polypropylene glycol (PPG) chains, mixed polyethylene/polypropylene glycol chains, radioactive isotopes, steroids, pharmaceutical compounds, lipids, peptides, glycans (including oligo- and polysaccharides), nucleotides (including oligo- and polynucleotides) and peptide tags. Examples of suitable fluorophores are for example all kinds of Alexa Fluor (e.g. Alexa Fluor 555), cyanine dyes (e.g. Cy3 or Cy5), coumarin derivatives, fluorescein, rhodamine, allophycocyanin, chromomycin, and so on. Examples of suitable peptide tags include FLAG or HIS tags. An example of a suitable glycan is concanavalin. Preferably, the label is selected from the group comprising fluorophores, biotin, polyethylene glycol chains, polypropylene glycol chains, mixed polyethylene/polypropylene glycol chains, radioactive isotopes, steroids, pharmaceutical compounds, lipids, peptides, glycans, nucleotides and peptide tags.

Functional group Q may be connected to the label directly, or indirectly via a linker or linking unit. Linking units are well know in the art, and have the general structure Q-S-Q, wherein Q is as defined above, and S is selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ aryl alkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups may be substituted, and optionally said groups may be interrupted by one or more heteroatoms, preferably 1 to 100 heteroatoms, said heteroatoms preferably being selected from the group consisting of O, S and $NR^6$, wherein $R^6$ is defined as above. Most preferably, the heteroatom is O.

Examples of suitable linking units include, but are not limited to, (poly)ethylene glycol diamines (such as for example 1,8-diamino-3,6-dioxaoctane or equivalents comprising longer ethylene glycol chains), polyethylene glycol or polyethylene oxide chains, polypropylene glycol or polypropylene oxide chains, 1,x-diaminoalkanes wherein x is the number of carbon atoms in the alkane, and the like. Another class of suitable linkers comprises cleavable linkers. Cleavable linkers are well known in the art.

In a preferred embodiment, the invention relates to a conjugate, wherein a compound of the Formula (IIa), (IIb) and/or (IIc) is conjugated to a label via a functional group Q. In a further preferred embodiment, the conjugated compound of the Formula (IIa), (IIb) and/or (IIc) is a compound wherein p is 1 and L is $CH_2$. $R^1$ and/or $R^3$ are preferably H. In another embodiment, n is 0 (Q, n, p, L, $R^1$ and $R^3$ as defined above). Most preferably, p is 1, L is $CH_2$, $R^1$ is H, $R^3$ is H and n is 0.

In another embodiment, the invention relates to a conjugate, wherein a compound of the Formula (IIIa), (IIIb) and/or (IIIc) is conjugated to a label via a functional group Q. In a further embodiment, the conjugated compound of the Formula (IIIa), (IIIb) and/or (IIIc) is a compound wherein p is 1 and L is $CH_2$. In yet another embodiment, p is 0, thus functional group Q is bonded directly to the N-atom. $R^1$ is preferably H. In another embodiment, n is 0 (Q, n, p, L, R and R as defined above). In a most preferred embodiment, p is 1, L is $CH_2$, $R^1$ is H and n is 0. In an alternative most preferred embodiment, p is 0, $R^1$ is H and n is 0.

In yet another embodiment, the invention relates to a conjugate, wherein a compound of the Formula (IVa), (IVb) and/or (IVc) is conjugated to a label via a functional group Q. In a preferred embodiment, the conjugated compound of the Formula (IVa), (IVb) and/or (IVc) is a compound wherein p is 1 and L is $CH_2$. $R^1$ and/or $R^3$ are preferably H, and Y is preferably C(O) or O. In another embodiment, n is 0 (Q, n, p, L, $R^1$ and $R^3$ as defined above). In a most preferred embodiment Y is O or C(O), p is 1, L is $CH_2$, $R^1$ is H, $R^3$ is H and n is 0. In another most preferred embodiment Y is O or C(O), p is 0, $R^1$ is H, $R^3$ is H and n is 0.

In addition, the invention relates to a conjugate, wherein a compound of the Formula (Va), (Vb) and/or (Vc) is conjugated to a label via a functional group Q. In a preferred embodiment, the conjugated compound of the Formula (Va), (Vb) and/or (Vc) is a compound wherein p is 1 and L is $CH_2$. $R^1$ preferably is H. Y is preferably C(O). In another embodiment, n is 0 (Q, n, p, L, Y, $R^1$ and $R^3$ as defined above). In a most preferred embodiment Y is C(O), p is 1, L is $CH_2$, $R^1$ is H and n is 0. In another most preferred embodiment Y is C(O), p is 0, $R^1$ is H and n is 0.

The invention also relates to a conjugate, wherein a compound of the Formula (VIa), (VIb) and/or (VIc) is conjugated to a label via a functional group Q. In a preferred embodiment, $R^1$ is H. In another preferred embodiment, p is 0, i.e. Q is bonded directly to the aryl group.

The present invention also relates to the use of a conjugate according to the invention for bioorthogonal labeling, imaging or modification, such as for example surface modification, of a target molecule.

Synthesis Method

It is a further aspect of the present invention to provide a synthesis method for compounds of the formula (Ia), (Ib) and (Ic). The invention thus relates to a method for preparing a compound of the general Formula (Ia), (Ib) or (Ic), the method comprising the steps of:

(a) Introduction of a fused 3- or 4-membered ring to a cyclooctadiene of the Formula (VIIa), (VIIb) or (VIIc):

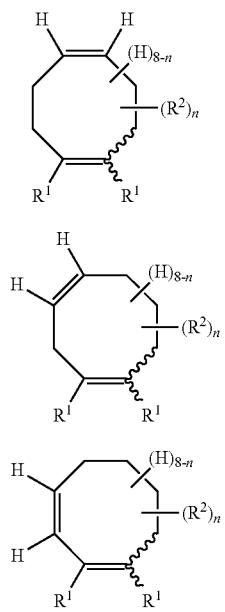

wherein:
n=0 to 8;
R$^1$ is independently selected from the group consisting of hydrogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups; and
R$^2$ is independently selected from the group consisting of halogen, —OR$^6$, —NO$_2$, —CN, —S(O)$_2$R$^6$, C$_1$-C$_{12}$ alkyl groups, C$_1$-C$_{12}$ aryl groups, C$_1$-C$_{12}$ alkylaryl groups and C$_1$-C$_{12}$ arylalkyl groups, wherein the alkyl groups, aryl groups, alkylaryl groups and arylalkyl groups are optionally substituted, and wherein R$^6$ is independently selected from the group consisting of hydrogen, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups,
to form a bicyclic cyclooctene compound,
(b) Bromination of the obtained bicyclic cyclooctene compound to form a bicyclic cyclooctane compound, and
(c) Dehydrobromination of the obtained bicyclic cyclooctane compound to form a compound of the general Formula (Ia), (Ib) or (Ic).

The cyclooctadiene of the formula (VIIa), (VIIb) or (VIIc) in step (a) may be a cis,cis- or a cis,trans-cyclooctadiene. In one embodiment, the cyclooctadiene is a cic,cis-cyclooctadiene. In a second embodiment, the cyclooctadiene is a cis,trans-cyclooctadiene. In other words, the double bond comprising the R$^1$-substituents may have the E- or the Z-configuration.

In a preferred embodiment R$^1$ is H. In another preferred embodiment, n is 0. In yet another preferred embodiment R$^1$ is H and n is 0.

Functional group Q may be introduced at any point in the synthesis method. For example, the functional group may be introduced during step (a), the formation of the bicyclic cyclooctene compound. The functional group may also be introduced in an additional step, for example before or after the bromination step (b) or after the dehydrobromination step (c). As will be clear to a person skilled in the art, the strategy employed for the introduction of the functional group depends entirely on the nature of the specific functional group that needs to be introduced.

Obviously, the method of choice for step (a), the introduction of a fused 3- or 4-membered ring onto a cyclooctadiene of the formula (VIIa), (VIIb) or (VIIc), depends on the type of 3- or 4-membered ring that is introduced. A 3-membered ring comprising a N-atom may for example be fused to the cyclooctadiene via reaction with a nitrene-comprising compound to form compounds of the Formula (IIIa), (IIIb) or (IIIc). The introduction of a 4-membered ring to the cyclooctadiene to form compounds of the Formula (IVa), (IVb) or (IVc) wherein Y is C(O) may for example be accomplished by reaction of the cyclooctadiene with a ketene-comprising compound. The introduction of a 4-membered ring comprising a N-atom to the cyclooctadiene to form compounds of the Formula (Va), (Vb) or (Vc) wherein Y is C(O), i.e. β-lactam comprising compounds, may be accomplished via reaction of the cyclooctadiene with an (activated) isocyanate. Subsequent hydrogenation results in compounds of the Formula (Va), (Vb) or (Vc) wherein Y is CH$_2$. Compounds of the Formula (VIa), (VIb) or (VIc) may for example be prepared via reaction of the cyclooctadiene with a (substituted) benzyne compound.

Step (b), bromination of a cyclooctene compound, and step (c), dehydrobromination of a cyclooctane compound, are considered standard organic transformations that are well known to a person skilled in the art.

The present inventors found that for example compounds of the Formula (IIa), (IIb) or (IIc) can be easily and rapidly prepared in good yield from readily available starting materials. The present invention therefore also relates to a method for preparing a compound of the Formula (IIa), (IIb) or (IIc), the method comprising the steps of:
(a) Cyclopropanation of a cyclooctadiene of the Formula (VIIa), (VIIb) or (VIIc):

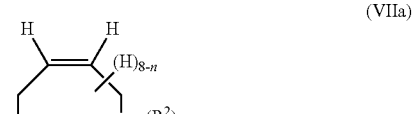

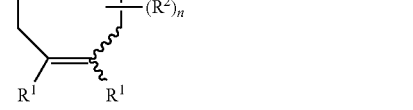

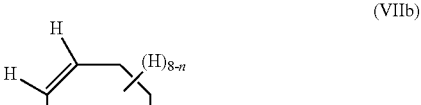

wherein n, R$^1$ and R$^2$ are as defined above to form a bicyclic cyclooctene compound, (b) Bromination of the obtained bicyclic cyclooctene compound to form a bicyclic cyclooctane compound, and
(c) Dehydrobromination of the obtained bicyclic cyclooctane compound to form a compound of the Formula (IIa), (IIb) or (IIc).

The cyclooctadiene of the Formula (VIIa), (VIIb) or (VIIc) in step (a) may be a cis,cis- or a cis,trans-cyclooctadiene. In one embodiment, the cyclooctadiene is a cic,cis-cyclooctadiene. In another embodiment, the cyclooctadiene is a cis,trans-cyclooctadiene. In other words, the double bond comprising the $R^1$-substituents may have the E- or the Z-configuration.

In a preferred embodiment $R^1$ is H. In another preferred embodiment, n is 0. In yet another preferred embodiment $R^1$ is H and n is 0.

Also in this case, functional group Q may be introduced in an additional step, for example before or following bromination step (b), or following dehydrobromination step (c). Step (a), the cyclopropanation of a cyclooctadiene may for example be achieved by reaction of a carbene, carbenoid or a carbene precursor with the cyclooctadiene, optionally in the presence of a catalyst. Step (b) and (c) are standard organic transformations that are well known to the person skilled in the art.

As an example, a compound of the Formula endo-(a), wherein p is 1, L is $CH_2$, Q is OH, n is 0, and $R^1$ and $R^3$ are H (endo-9-(hydroxymethyl)bicyclo[6.1.0]non-4-yne), may be synthesised in good yield in only 4 steps in a very short time (only 1-2 days). Yet another advantage of the synthesis method according to the present invention is that there only is a limited need for chromatographic purification, thus reducing the total time needed for the total synthesis.

Modification of Target Molecules

The conjugates according to the present invention are successfully applied in bioorthogonal labeling, imaging or modification, including surface modification, of target molecules such as for example proteins, lipids and glycans. The present invention therefore also relates to a method for the modification of a target molecule, wherein a conjugate according to the present invention is reacted with a compound comprising a 1,3-dipole or a 1,3-(hetero)diene. As an example, the strain-promoted cycloaddition of a cycloalkyne with an azide (SPAAC) or with a nitrone (SPANC) was depicted in Scheme 1. The reaction of a cyclooctyne with a 1,3-(hetero)diene is known as a (hetero) Diels-Alder reaction. These reactions are also referred to as metal-free click reactions.

1,3-Dipolar compounds are well known in the art (cf. for example F. A. Carey and R. J. Sundberg, Advanced Organic Chemistry, Part A: Structure and Mechanisms, 3$^{rd}$ Ed., 1990, p. 635-637), and include nitrile oxides, azides, diazomethane, nitrones, nitrilamines, etc. Preferably, the compound comprising a 1,3-dipole is an azide-comprising compound, a nitrone-comprising compound or a nitrile oxide-comprising compound.

(Hetero) Diels-Alder reactions and 1,3-(hetero)dienes are also well known in the state of the art. Examples of 1,3-dienes include, amongst others, 1,3-butadiene, 1,3-cyclopentadiene, 1,3-cyclohexadiene, furan, pyrrole, and their substituted varieties. Examples of 1,3-heterodienes include amongst others 1-oxa-1,3-butadiene, 1-aza-1,3-butadiene, 2-aza-1,3-butadiene, 3-aza-1,3-butadiene, and their substituted varieties.

A large variety of target molecules, i.e. compounds comprising a 1,3-dipole or a 1,3-(hetero)diene, may be modified by the method according to the invention. Suitable target molecules are well known in the art and include, but are not limited to, biomolecules such as for example proteins, peptides, glycans, lipids, nucleic acids, enzymes, hormones, and the like. In principle, any compound comprising a 1,3-dipole or a 1,3-(hetero)diene may be suitable as a target molecule.

Applications of the method for the modification of target molecules according to the present invention include, but are by no means limited to, diagnostic and therapeutic applications, cell labeling of living cells, for example MV3 cells, fibroblasts, Jurkat, CHO or HEK cells, modification of biopolymers (proteins, lipids, nucleic acids, glycans), enrichment of proteins and glycans for mass spectrometric analysis, tuning of polymer properties, surface modifications etc.

In one embodiment, the reaction of the conjugate is performed in vitro. In a preferred embodiment, the reaction is performed in vivo, i.e. under physiological conditions.

The conjugates according to the present invention that are applied in the modification of a target molecule are described above in great detail. One of the large advantages of these conjugates is that they may be applied both in vivo and in vitro. In addition, the here described conjugates suffer less from undesired a specific lipophilic interactions, and show good reaction kinetics in metal-free click reactions. Another advantage is that the here described conjugates are easily synthesized and amenable to simple and straightforward modification of various parts of the conjugate. This makes it possible to "fine tune" a conjugate for a specific application, and optimise reaction kinetics for this application.

In a preferred embodiment, a compound of the Formula (IIa), (IIb) and/or (IIc), or a conjugate thereof as described above, is reacted with a compound comprising a 1,3-dipole or a 1,3-(hetero)diene. For example the cycloaddition of (IIa) with benzyl azide in aqueous conditions proceeds rapidly and cleanly to the corresponding triazole adducts with excellent reaction kinetics (k=0.09-0.28 $M^{-1}$ $s^{-1}$, depending on the solvent). Reaction kinetics for the cycloaddition of (IIa) with C-benzylamide-N-methylnitrone are even higher (k=1.25 $M^{-1}$ $s^{-1}$). Surprisingly, the reaction kinetics are similar for both exo-(IIa) and endo-(IIa), indicating that the stereochemistry at the C-9 position of compound (IIa) has little influence on reactivity. Consequently, a mixture of the exo- and endo-compounds according to the invention may be applied in some applications, avoiding the need for separation of the exo- and endo-compounds and even further simplifying the synthesis of the compounds according to the invention.

Additional applications of the method according to the present invention include for example the ligation of a fluorophore conjugate wherein (IIa) is conjugated with Alexa Fluor 555 to a viral plasmid protein containing a single azide, and the detection of cell surface glycans by means of the chemical reporter strategy.

Pharmaceutical Composition

Finally, the invention relates to a composition comprising a conjugate according to the invention, further comprising a pharmaceutically acceptable carrier. A wide variety of suitable pharmaceutically acceptable carriers are known in the art (cf. for example R. C. Rowe, P. J. Sheskey and P. J. Weller (Eds.), Handbook of Pharmaceutical Excipients, 4$^{th}$ Ed. 2003).

EXAMPLES

Example 1

Synthesis of Exo- and Endo-IIa.2

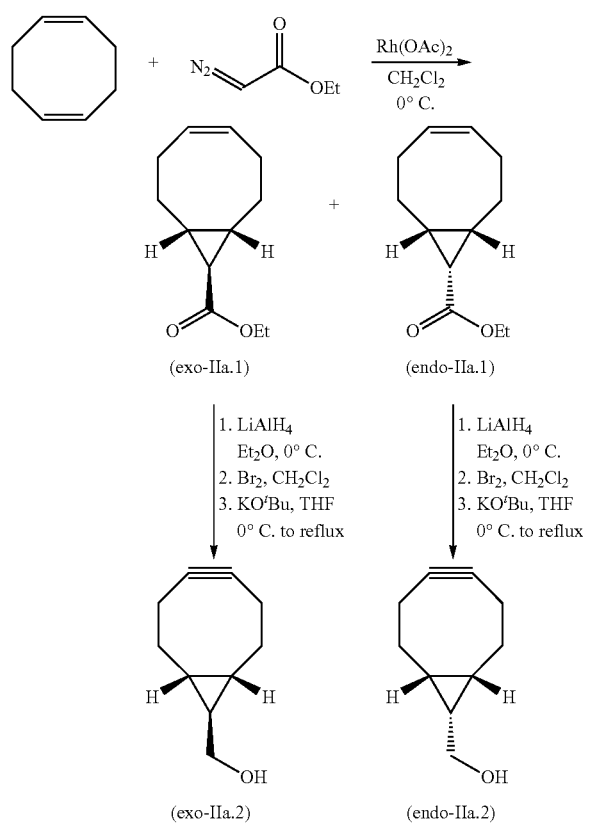

In the first step, ethyl diazoacetate was slowly added to a solution in dichloromethane of a large excess (8 equiv.) of 1,5-cyclooctadiene in the presence of rhodium acetate, leading to the diastereomeric compounds exo-IIa.1 and endo-IIa.1 in a ratio of 2:1 (combined yield of 82%). After straightforward separation by silica gel, first the endo-isomer of IIa.1 was converted into alcohol IIa.2 following a straightforward three-step procedure of reduction, bromination and elimination. Thus, ester reduction of endo-IIa.1 with LiAlH$_4$ (30 min) gave a crude intermediate alcohol (30 min) that was pure enough for bromination without intermediate purification (30 min). It must be noted that temporary protection of the alcohol, as in the synthesis of DIBO, is not required. Finally, the resulting dibromide was subjected to excess KO$^t$Bu in THF (0° C.→reflux, 2 h), affording the desired 9-(hydroxymethyl)-bicyclo[6.1.0]non-4-yne endo-IIa.2 in 61% isolated yield for the three steps from endo-IIa.1. A similar sequence of events, that can be executed in a single day with only one chromatographic purification, afforded the diastereomeric exo-isomer of IIa.2 in 53%.

Example 2

Reaction Kinetics

The reaction kinetics for cycloaddition with the prototypical azide benzyl azide were investigated. Thus, compound endo-IIa.2 was dissolved in a 3:1 mixture of CD$_3$CN and D$_2$O and mixed with benzyl azide at a final concentration of 18 mM. Chemical conversion was followed with proton NMR by integration of diagnostic peaks and indicated that endo-IIa.2 reacted rapidly and cleanly to the expected triazole adducts. Calculation of second-order reaction kinetics showed a rate constant of 0.12 similar value of 0.10 M$^{-1}$ s$^{-1}$ was determined for exo-IIa.2, indicating that the stereochemistry at the C-9 position has little influence on reactivity, with only a slightly higher rate for the endo-configured compounds. A significant solvent effect was noticed because the same cycloaddition reaction in a 1:2 mixture of CD$_3$CN and D$_2$O gave rate constants of 0.28 and 0.25 M$^{-1}$ s$^{-1}$ for endo-IIa.2 and exo-IIa.2, respectively.

Example 3

Bicyclo[6.1.0]non-4-yne (BCN) Conjugates

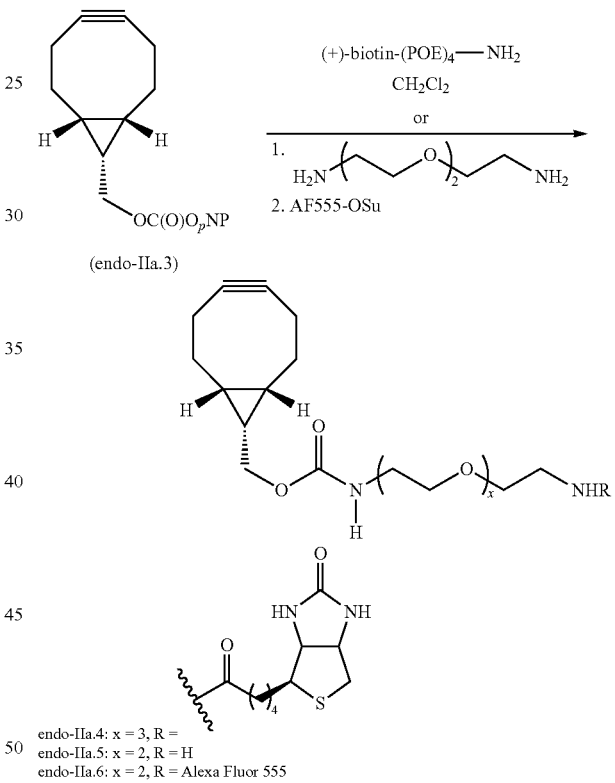

endo-IIa.4: x = 3, R = 
endo-IIa.5: x = 2, R = H
endo-IIa.6: x = 2, R = Alexa Fluor 555

BCN Conjugated to Biotin (IIa.4)

The alcohol moiety of endo-IIa.1 was converted into a p-nitrophenyl (pNP) carbonate as in IIa.3. Subsequent reaction with biotin-(POE)$_3$-NH$_2$ led to BCN-biotin conjugate IIa.4 (69% yield).

BCN Conjugated to Alexa Fluor 555 (IIa.6)

Alternatively, compound IIa.3 was reacted with 1,8-diamino-3,6-dioxaoctane to give amino-terminated BCN-probe IIa.5, that was converted into the fluorophore conjugate IIa.6 upon reaction with commercial Alexa Fluor 555 hydroxysuccinimide ester.

Alternatively, compound IIa.3 was reacted with 1,5-diaminopentane to give a more lipophilic amino-terminated BCN-probe.

Example 4

Reaction of IIa.6 with Azide-Labeled Capsid Protein (SPAAC Labeling)

The capsid protein was prepared to contain only a single azide functionality per molecule, which—after assembly of the capsid—is located on the inside surface of the capsid. The protein is dissolved in buffer (50 mM phosphate buffer pH 7.5; 1M NaCl) at a concentration of 1 mg/mL. Alexa Fluor 555-BCN conjugate IIa.6 was dissolved in water and 4 equivalents of the conjugate were added to the protein solution. The reaction mixture was incubated for 3 hours at RT before analysis.

The reaction product was analyzed on a 12% SDS-PAGE gel, of which a fluorescence image was recorded before staining with Coomassie-blue. In FIG. 1 the SDS-Page analyses of the reaction product (left) and of the blank reaction (right) are shown. The top part of FIG. 1 shows the Coomassie-blue staining, the bottom part shows the fluorescence image before staining with Coomassie-blue. These results clearly indicate that the Alexa Fluor 555-BCN conjugate was incorporated into the capsid protein.

Figure 2:
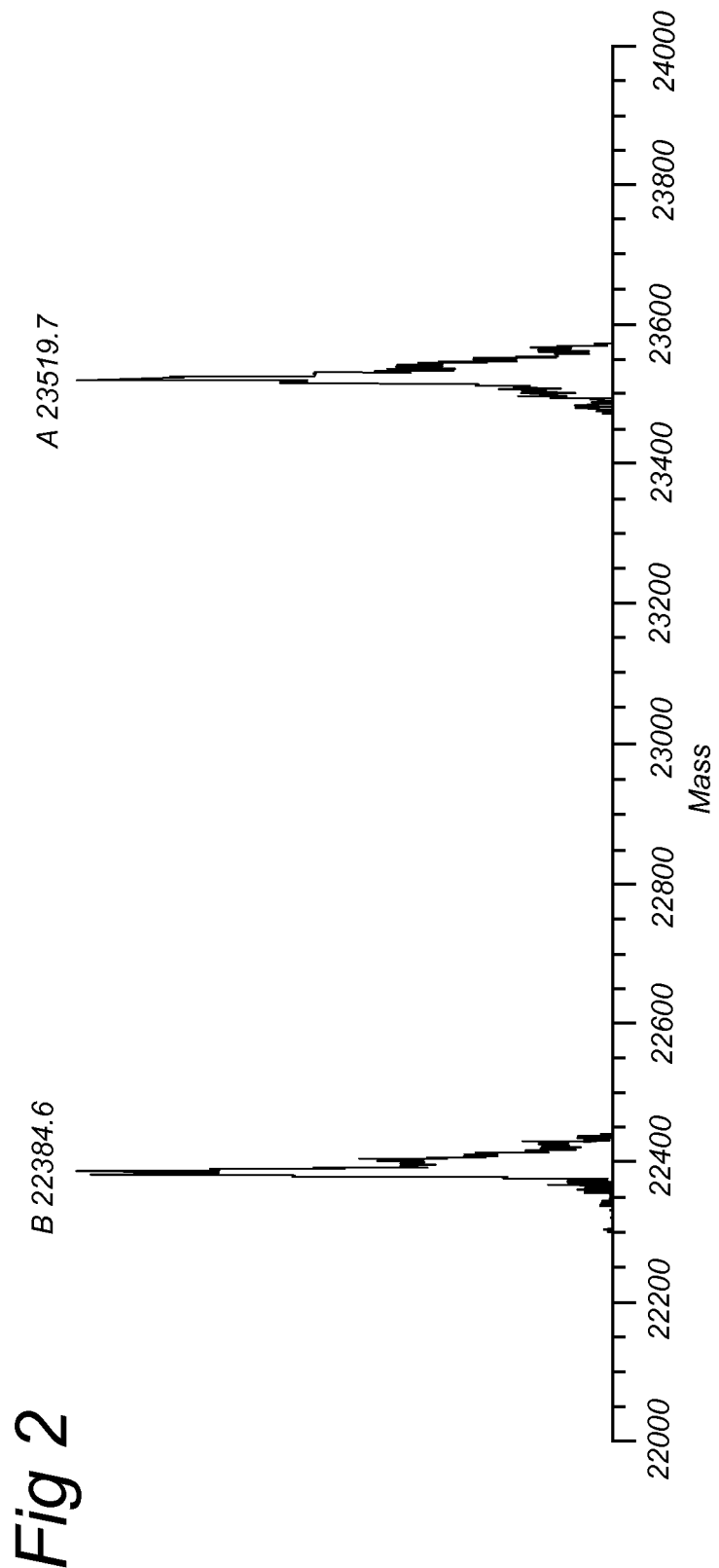
FIG. 2 depicts the ESI-TOF mass spectrum of capsid protein functionalized with a cyclooctyne conjugated to Alexa Fluor 555.

For mass analysis, the crude reaction mixture was dialyzed to 0.1% TFA in milliQ before analyzing it by electron-spray ionization time-of-flight (ESI-TOF) on a JEOL AccuTOF. FIG. 2 shows the ESI-TOF mass spectrum of capsid protein reacted with IIa.6. Peak B corresponds to the mass of unreacted capsid protein, while peak A corresponds to the reaction product. The mass difference between the peaks is 1135.1 (expected 1135), indicating that the single azide in the capsid protein has effectively reacted with the BCN-Alexa Fluor555 conjugate which has a mass of 1135.

Figure 3:
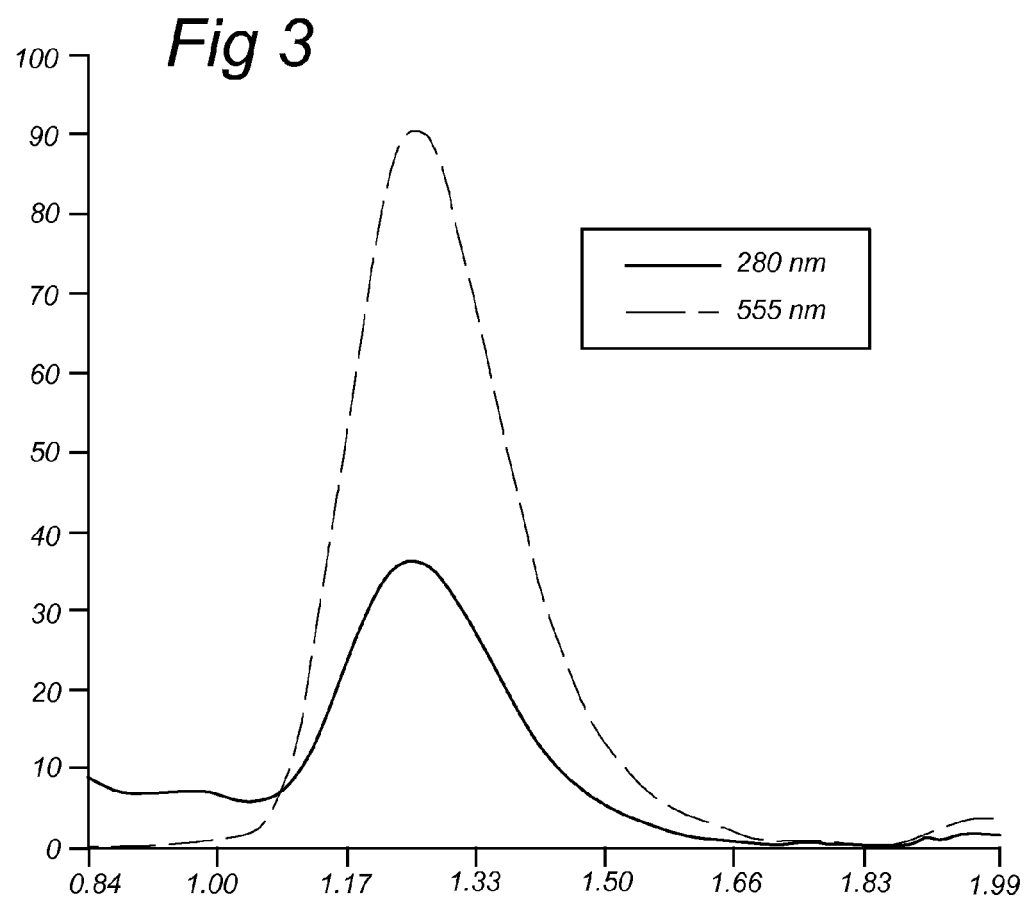
FIG. 3 depicts the FPLC analysis of capsin protein functionalized with a cyclooctyne conjugated to Alexa Fluor 555.

To test the self-assembly properties of the functionalized capsid protein, the crude reaction mixture was dialyzed to a buffer at pH 5.0 (50 mM NaOAc: 1 M NaCl; 10 mM $CaCl_2$), which should induce the formation of 28 nm sized spherical particles (B. J. M. Verduin, *FEES Lett.* 1974, 45, 50-54, incorporated by reference). After assembly of the capsids by dialysis, the reaction mixture was analyzed by FPLC. The size exclusion analysis on a Superpose 6 column is shown in FIG. 3. The absorption peak at 280 nm at an elution volume of 1.2 ml indicates the formation of 28 nm-sized capsids, and the overlapping absorbance at 555 nm shows that the Alexa dye, and thus IIa.6, is present in the capsids.

Example 5

Reaction of IIa.2 with Nitrone-Labeled FRATtide Protein (SPANC Labeling)

FRATtide (15.6 µg, 3.4 nmol, 34 µM) was dissolved in 0.1 M $NH_4OAc$ buffer pH 6.9 (100 µL) and $NaIO_4$ (1.1 µg, 5.5 nmol. 48 µM) was added. The reaction was allowed to take place at room temperature for 40 min and p-methoxybenzenethiol (9.2 µg, 66.0 nmol, 565 µM) was added. The mixture was shaken for 2 h at 25° C. and p-anisidine (13.5 µg, 109.3 µmol, 845 µM), N-methylhydroxylamine hydrochloride (18.2 µg, 218.6 nmol, 1.5 mM), and BCN—OH II.a2 (41.1 µg, 273.3 nmol, 1.8 mM) were added. Finally, the reaction mixture was shaken at 25° C. for 24 h to give the desired conjugate.

Progress of the reaction was monitored by mass spectrometry (Accu-TOF). The molecular ion peak at 4533.8 Da, corresponding to the FRATtide protein, disappeared upon treatment with sodium periodate, whereas a molecular ion peak at 4534.8, corresponding to the methyl hemiacetal, appeared. Upon treatment with N-methylhydroxylamine and BCN—OH, a molecular ion peak appeared at 4681.4 Da, corresponding to FRATtide protein nitrone derivative that has reacted with BCN—OH IIa.2, as the main peak (after deconvolution).

Example 6

Cell-Surface Labeling

The usefulness of biotin-conjugate IIa.4 for bioorthogonal labeling purposes was investigated by detection of cell surface glycans by means of the chemical reporter strategy. N-Azidoacetylmannosamine (ManNAz) was metabolically incorporated in MV3 cells, and detected by FACS and confocal microscopy.

Cell Culture Procedure

Invasive and metastatic human melanoma cells (MV3) were maintained in culture medium RPMI 1640, containing 10% fetal calf serum, penicillin/streptomycin (each 50 U/ml) in a 5% $CO_2$ water-saturated atmosphere.

Cell Surface Azide Labeling

MV3 cells were cultured for 6 days in the absence or presence of $Ac_4ManNAz$ (50 µM). Medium and compound change was performed after 3 days. Cell adhesion and morphology was analyzed with a bright field microscope prior to the advanced studies. For live-cell labeling, cells were detached by EDTA (1 mM), washed and centrifuged three times (PBS, 300×G rpm, 5 min, 4° C.), resuspended in PBS and incubated in BCN-biotin (IIa.4) (60 µM), DIBO-biotin (60 µM) or buffer (1 h, 20° C.), washed three times (PBS, 300×G, 2 min, 4° C.), resuspended in ice-cold PBS containing AlexaFluor488-conjugated streptavidin (5 µg/ml, Invitrogen; final volume 200 µl). After incubation (30 min, 4° C.), cells were washed three times, resuspended in PBS (200 µl, 4° C.) for further biological analysis.

Flow Cytometry

Flow cytometry was performed on a BD Biosciences FACS-Calibur flow cytometer using the 488 nm argon laser and data were analyzed with FCS Express version 3 research edition (De Novo Software, Los Angeles, Calif.). Per sample, $2 \times 10^4$ morphologically intact cells were analyzed in the presence of propidium iodide (2.5 µg/ml).

Figure 4:
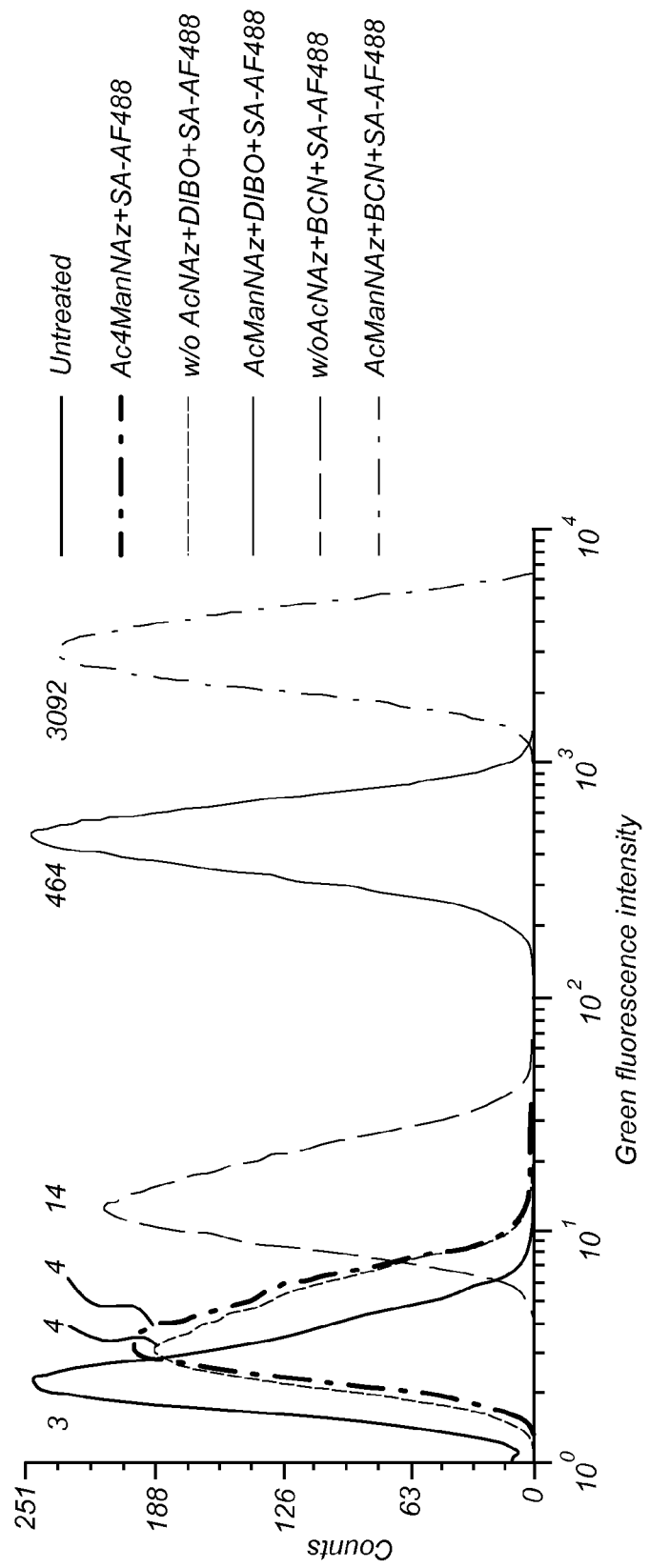
FIG. 4 depicts the cell surface fluorescence on intact MV3 cells after metabolic incorporation of Ac₄ManNAz, labeling with DIBO- or BCN-biotin, and detection with AlexaFluor488-conjugated streptavidin as determined with flow cytometry.

In FIG. 4, the cell surface fluorescence on intact MV3 cells after metabolic incorporation of $Ac_4ManNAz$, labeling with DIBO- or BCN-biotin and detection with AlexaFluor488-conjugated streptavidin is shown. Analysis by flow cytometry indicates a more than 100-fold increase in fluorescence intensity for labeling with BCN-biotin or DIBO-biotin, followed by detection with AlexaFluor488-conjugated streptavidin, with neglible background levels of fluorescence when cells are not incubated with $Ac_4ManNAz$.

Figure 5A:
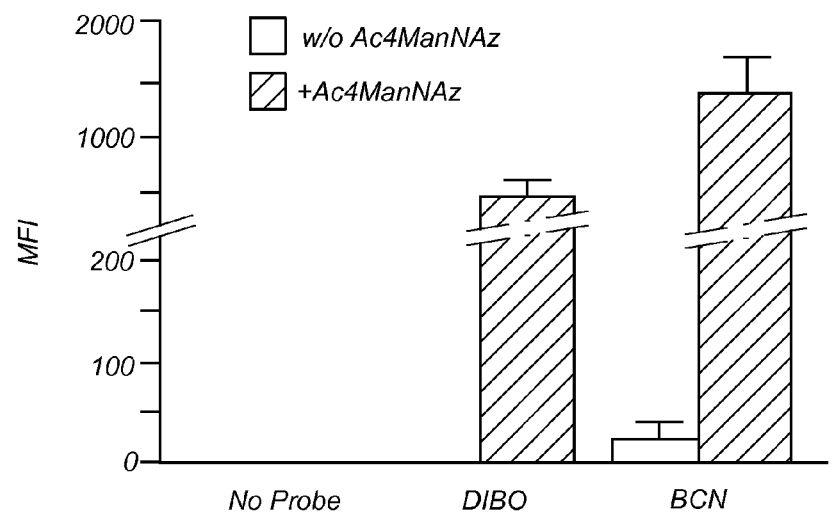
FIG. 5 depicts the fluorescence intensities and cell viability of MV3 cells after metabolic incorporation of Ac₄ManNAz, labeling with DIBO- or BCN-biotin, and detection with AlexaFluor488-conjugated streptavidin.
Figure 5B:
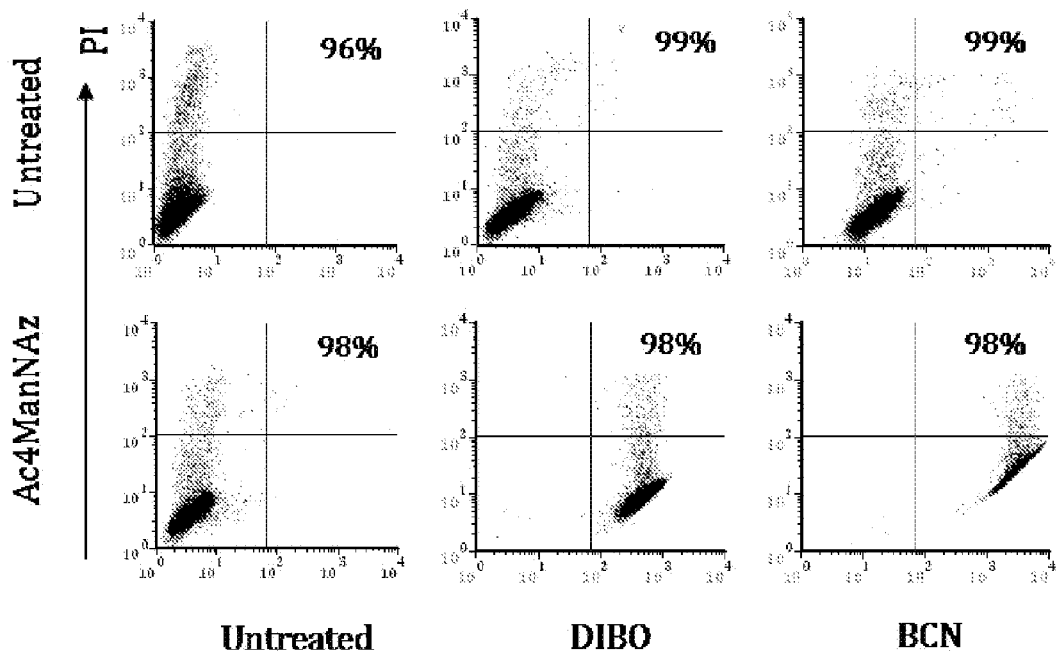

FIG. 5 shows the fluorescence intensities and cell viability of MV3 cells after metabolic incorporation of $Ac_4ManNAz$, labeling with DIBO- or BCN-biotin, and detection with AlexaFluor488-conjugated streptavidin. In FIG. 5A the mean intensities for green fluorescence (AlexaFluor488) and standard deviations (SD) from four independent experiments are shown, in FIG. 5B the intact cell viability after glycan labeling. Green fluorescence (AlexaFluor488) and propidium iodide (PI) labels were used. Numbers indicate the percentage of PI-negative, viable cells. From FIG. 5A, it can be concluded that both BCN and DIBO are effectively labeling cells that were prior exposed to $Ac_4ManNAz$, with a higher efficiency of labeling with BCN-biotin. FIG. 5B shows that cells, whether untreated, treated with BCN or treated with DIBO, showed high viability (>98% in all cases).

Confocal Microscopy

Cell surface glycans were labeled with BCN-biotin or DIBO-biotin and next with AlexaFluor488-conjugated streptavidin. After labeling, cells were resuspended in normal culture medium, transferred in a 6-well plate and incubated for 30 min at 37° C. Life cell imaging of MV3 cells was performed on a Olympus FV1000 confocal laser scanning microscope with an argon 488 laser, excitation 488 nm, emission 520 nm and a 40× magnification at room temperature.

Figure 6:
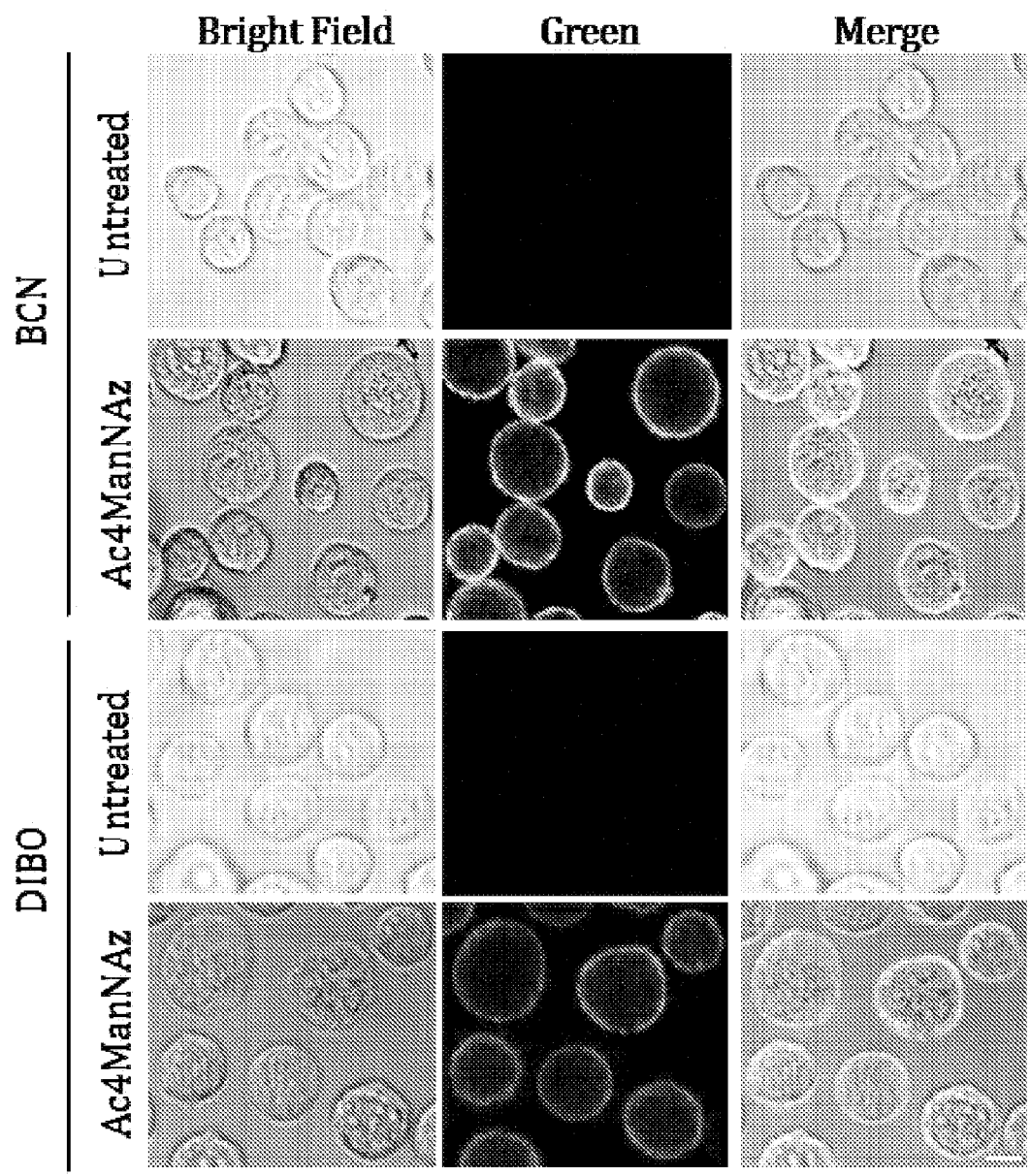
FIG. 6 depicts representative confocal images of labeled cells, previously cultured in absence or presence of Ac₄ManNAz (50 µM), labeling with DIBO- or BCN-biotin, and detection with AlexaFluor488-conjugated streptavidin.

FIG. 6 shows representative confocal images of labeled cells, previously cultured in absence or presence of $Ac_4ManNAz$ (50 μM). The confocal images clearly show that the cell surface of MV3-cells become fluorescent upon incubation of the cells with $Ac_4ManNAz$ followed by detection of cell surface glycans with BCN-biotin or DIBO-biotin and then AlexaFluor488-conjugated streptavidin, but not without incubation with $Ac_4ManNAz$.

Example 7

Synthesis of IIa.7

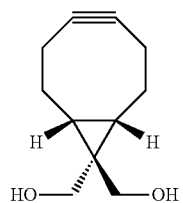

(1R,8S,Z)-Diethyl bicyclo[6.1.0]non-4-ene-9,9-dicarboxylate (IIa.8)

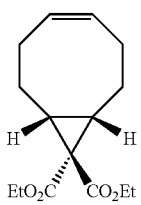

To a solution of 1,5-cyclooctadiene (5.27 mL, 43.0 mmol) and $Rh_2(OAc)_4$ (100 mg, 0.23 mmol) in $CH_2Cl_2$ (5 mL) was added dropwise in 3 h a solution of diethyl diazomalonate (1.0 g, 5.37 mmol) in $CH_2Cl_2$ (5 mL). This solution was stirred for 24 h at rt. The $CH_2Cl_2$ was evaporated and the excess of cyclooctadiene was removed by filtration over a glass filter filled with silica (cluens: heptane). The filtrate was concentrated in vacuo and the residue was purified by column chromatography on silica gel (EtOAc:heptane, 1:10) to afford IIa.8 (1.03 g, 72%).

$^1$H NMR (CDCl$_3$, 400 MHz): δ 5.65-5.57 (m, 2H), 4.10 (2×q, J=7.2 Hz, 4H), 2.41-2.29 (m, 2H), 2.15-2.06 (m, 3H), 1.83-1.70 (m, 3H), 1.31-1.23 (2×t, J=7.2 Hz, 6H).

(1R,8S,Z)-Bicyclo[6.1.0]non-4-ene-9,9-diyldimethanol (IIa.9)

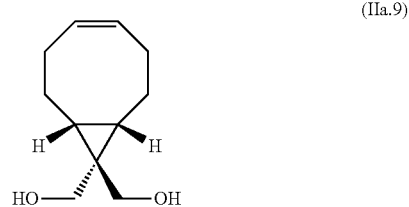

To a suspension of LiAlH$_4$ (103 mg, 2.70 mmol) in Et$_2$O (10 mL) was added dropwise at 0° C. a solution of IIa.8 (400 mg, 1.50 mmol) in Et$_2$O (10 mL). Water was added carefully until the grey solid had turned into white. Then Na$_2$SO$_4$ (2 g) was added, the solid was filtered off and washed thoroughly with Et$_2$O (100 mL). The filtrate was concentrated in vacuo. The residue was purified by column chromatography on silica gel (EtOAc:heptane, 3:1) to afford IIa.9 as a white solid (190 mg, 69%).

$^1$H NMR (CDCl$_3$, 400 MHz): δ 5.66-5.58 (m, 2H), 3.88 (d, J=4.8 Hz, 2H), 3.58 (d, J=4.8 Hz, 2H), 2.43-2.35 (m, 2H), 2.20-1.99 (m, 6H), 1.71-1.57 (m, 2H), 0.95-0.88 (m, 2H).

((1R,8S)-4,5-Dibromobicyclo[6.1.0]nonane-9,9-diyl)dimethanol (IIa.10)

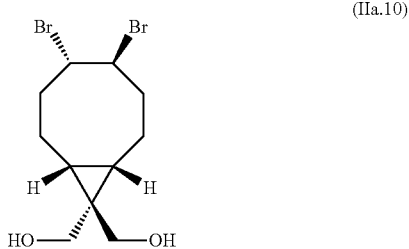

The diol IIa.9 (145 mg, 0.796 mmol) was dissolved in CH$_2$Cl$_2$ (5 mL). At 0° C. a solution of Br$_2$ (45 μL, 0.875 mmol) in CH$_2$Cl$_2$ (1 mL) was added dropwise until the yellow color persisted. The reaction mixture was quenched with a 10% Na$_2$S$_2$O$_3$-solution (5 mL), and extracted with CH$_2$Cl$_2$ (2×20 mL). The organic layer was dried (Na$_2$SO$_4$) and concentrated in vacuo. The residue was purified by column chromatography on silica gel (EtOAc:heptane, 5:1) afford IIa.10 (235 mg, 86%) as a white solid.

$^1$H NMR (CDCl$_3$, 400 MHz): δ 4.87-4.78 (m, 2H), 3.96-3.88 (m, 2H), 3.60 (d, J=5.2 Hz, 2H), 2.75-2.63 (m, 2H), 2.32-2.22 (m, 3H), 2.20-2.13 (m, 1H), 2.05-1.94 (m, 2H), 1.74-1.57 (m, 2H), 1.13-0.99 (m, 2H).

(1R,8S)-Bicyclo[6.1.0]non-4-yn-9,9-diyldimethanol (IIa.7)

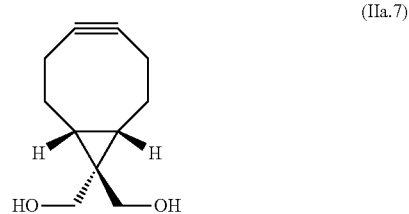

To a solution of the dibromide IIa.10 (100 mg, 0.292 mmol) in THF (5 mL) was added dropwise at 0° C. a solution of KO$_t$Bu (1.29 mL, 1 M in THF, 1.29 mmol). Then the solution was refluxed for 1.5 h. After cooling down to rt the mixture was quenched with saturated NH$_4$Cl-solution (20 mL), and extracted with CH$_2$Cl$_2$ (3×20 mL). The organic layer was dried (Na$_2$SO$_4$) and concentrated in vacuo. The residue was purified by column chromatography on silica gel (EtOAc) to afford IIa.7 (24 mg, 46%) as a white solid.

$^1$H NMR (CDCl$_3$, 400 MHz): δ 3.89 (bs, 2H), 3.63 (bs, 2H), 2.58 (bs, 2H), 2.34-2.20 (m, 6H), 1.68-1.59 (m, 2H), 0.89-0.82 (m, 2H).

The invention claimed is:

1. A compound of the Formula (IIa):

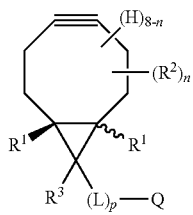

(IIa)

wherein:
n is 0 to 8;
p is 0 or 1;
R$^3$ is selected from the group consisting of [(L)$_p$-Q], hydrogen, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups, the alkyl groups optionally being interrupted by one of more heteroatoms selected from the group consisting of O, N and S, wherein the alkyl groups, (hetero)aryl groups, alkyl (hetero)aryl groups and (hetero)arylalkyl groups are independently optionally substituted with one or more substituents independently selected from the group consisting of C$_1$-C$_{12}$ alkyl groups, C$_2$-C$_{12}$ alkenyl groups, C$_2$-C$_{12}$ alkynyl groups, C$_3$-C$_{12}$ cycloalkyl groups, C$_1$-C$_{12}$ alkoxy groups, C$_2$-C$_{12}$ alkenyloxy groups, C$_2$-C$_{12}$ alkynyloxy groups, C$_3$-C$_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S, wherein the silyl groups are represented by the formula (R$^4$)$_3$Si—, wherein R$^4$ is independently selected from the group consisting of C$_1$-C$_{12}$ alkyl groups, C$_2$-C$_{12}$ alkenyl groups, C$_2$-C$_{12}$ alkynyl groups, C$_3$-C$_{12}$ cycloalkyl groups, C$_1$-C$_{12}$ alkoxy groups, C$_2$-C$_{12}$ alkenyloxy groups, C$_2$-C$_{12}$ alkynyloxy groups and C$_3$-C$_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S;

L is a linking group selected from linear or branched C$_1$-C$_{24}$ alkylene groups, C$_2$-C$_{24}$ alkenylene groups, C$_2$-C$_{24}$ alkynylene groups, C$_3$-C$_{24}$ cycloalkylene groups, C$_5$-C$_{24}$ cycloalkenylene groups, C$_8$-C$_{24}$ cycloalkynylene groups, C$_7$-C$_{24}$ alkyl(hetero)arylene groups, C$_7$-C$_{24}$ (hetero)arylalkylene groups, C$_8$-C$_{24}$ (hetero)arylalkenylene groups, C$_9$-C$_{24}$ (hetero)arylalkynylene groups, the alkylene groups, alkenylene groups, alkynylene groups, cycloalkylene groups, cycloalkenylene groups, cycloalkynylene groups, alkyl(hetero)arylene groups, (hetero)arylalkylene groups, (hetero)arylalkenylene groups and (hetero)arylalkynylene groups optionally being substituted with one or more substituents independently selected from the group consisting of C$_1$-C$_{12}$ alkyl groups, C$_2$-C$_{12}$ alkenyl groups, C$_2$-C$_{12}$ alkynyl groups, C$_3$-C$_{12}$ cycloalkyl groups, C$_5$-C$_{12}$ cycloalkenyl groups, C$_8$-C$_{12}$ cycloalkynyl groups, C$_1$-C$_{12}$ alkoxy groups, C$_2$-C$_{12}$ alkenyloxy groups, C$_2$-C$_{12}$ alkynyloxy groups, C$_3$-C$_{12}$ cycloalkyloxy groups, halogens, amino groups, oxo and silyl groups, wherein the silyl groups can be represented by the formula (R$^4$)$_3$Si—, wherein R$^4$ is defined as above;

Q is a functional group selected from the group consisting of hydrogen, halogen, R$^6$, —CH=C(R$^6$)$_2$, —C≡CR$^6$, —[C(R$^6$)$_2$C(R$^6$)$_2$O]$_q$—R$^6$, wherein q is in the range of 1 to 200, —CN, —N$_3$, —NCX, —XCN, —XR$^6$, —N(R$^6$)$_2$, —$^+$N(R$^6$)$_3$, —C(X)N (R$^6$)$_2$, —C(R$^6$)$_2$XR$^6$, —C(X)R$^6$, —C(X)XR$^6$, —S(O)R$^6$, —S(O)$_2$R$^6$, —S(O)OR$^6$, —S(O)$_2$OR$^6$, —S(O)N(R$^6$)$_2$, —S(O)$_2$N(R$^6$)$_2$, —OS(O)R$^6$, —OS(O)$_2$R$^6$, —OS(O)OR$^6$, —OS(O)$_2$OR$^6$, —P(O)(R$^6$)(OR$^6$), —P(O)(OR$^6$)$_2$, —OP(O)(OR$^6$)$_2$, —Si(R$^6$)$_3$, —XC(X)R$^6$, —XC(X)XR$^6$, —XC(X)N(R$^6$)$_2$, —N(R$^6$)C(X)R$^6$, —N(R$^6$)C(X)XR$^6$ and —N(R$^6$)C (X)N(R$^6$)$_2$, wherein X is oxygen or sulphur and wherein R$^6$ is independently selected from the group consisting of hydrogen, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups;

R$^1$ is independently selected from the group consisting of hydrogen, C$_1$-C$_{24}$ alkyl groups, C$_6$-C$_{24}$ (hetero) aryl groups, C$_7$-C$_{24}$ alkyl(hetero)aryl groups and C$_7$-C$_{24}$ (hetero)arylalkyl groups; and R$^2$ is independently selected from the group consisting of halogen, —OR$^6$, —NO$_2$, —CN, —S(O)$_2$R$^6$, C$_1$-C$_{12}$ alkyl groups, C$_1$-C$_{12}$ aryl groups, C$_1$-C$_{12}$ alkylaryl groups and C$_1$-C$_{12}$ arylalkyl groups, wherein R$^6$ is as defined above, and wherein the alkyl groups, aryl groups, alkylaryl groups and arylalkyl groups are optionally substituted.

2. The compound according to claim 1, wherein n is 0.

3. The compound according to claim 1, wherein p is 1 and L is CH$_2$.

4. The compound according to claim 1, wherein Q is selected from the group consisting of —OR$^6$, —N(R$^6$)$_2$, —$^+$N(R$^6$)$_3$, —C(O)N(R$^6$)$_2$, —C(O)OR$^6$, —OC(O)R$^6$, —OC (O)OR$^6$, —OC(O)N(R$^6$)$_2$, —N(R$^6$)C(O)R$^6$, —N(R$^6$)C(O) OR$^6$ and —N(R$^6$)C(O)N(R$^6$)$_2$, wherein R$^6$ is as defined in claim 1.

5. The compound according to claim 1, wherein Q is —OH.

6. The compound according to claim 1, wherein R$_1$ is hydrogen.

7. The compound according to claim 1, wherein R$^3$ is hydrogen or [(L)$_p$-Q].

8. The compound according to claim 1, wherein p is 1, L is CH$_2$, Q is —OH, R$^1$ is hydrogen and R$^3$ is hydrogen or [(L)$_p$-Q].

9. The compound according to claim 2, wherein p is 1, L is CH$_2$, Q is —OH, R$^1$ is hydrogen, and R$^3$ is hydrogen or [(L)$_p$-Q].

10. A conjugate comprising a compound according to claim 1 conjugated to a label via a functional group Q, wherein the label is selected from the group comprising of fluorophores, biotin, polyethylene glycol chains, polypropylene glycol chains, mixed polyethylene/polypropylene glycol chains, radioactive isotopes, steroids, pharmaceutical compounds, lipids, peptides, glycans, nucleotides and peptide tags.

11. A method for preparing a compound according to claim 1, the method comprising:
(a) Cyclopropanation of a cyclooctadiene of the Formula (VIIa):

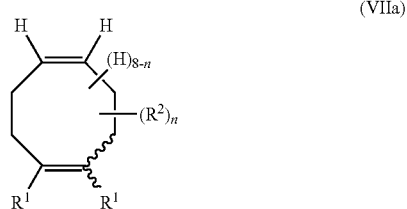

wherein:
n=0 to 8;
R$^1$ is independently selected from the group consisting of hydrogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups; and
R$^2$ is independently selected from the group consisting of halogen, —OR$^6$, —NO$_2$, —CN, —S(O)$_2$R$^6$, C$_1$-C$_{12}$ alkyl groups, C$_1$-C$_{12}$ aryl groups, C$_1$-C$_{12}$ alkylaryl groups and C$_1$-C$_{12}$ arylalkyl groups, wherein the alkyl groups, aryl groups, alkylaryl groups and arylalkyl groups are optionally substituted, and wherein R$^6$ is independently selected from the group consisting of hydrogen, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups,
to form a bicyclic cyclooctene compound,
(b) Bromination of the obtained bicyclic cyclooctene compound to form a bicyclic cyclooctane compound, and
(c) Dehydrobromination of the obtained bicyclic cyclooctane compound to form a compound according to claim 1.

12. A method for the modification of a target molecule, comprising reacting a conjugate according to claim 10 with a compound comprising a 1,3-dipole or a 1,3-(hetero)diene.

13. The method according to claim 12, wherein the compound comprising a 1,3-dipole is an azide-comprising compound, a nitrone-comprising compound, or a nitrile oxide-comprising compound.

14. A composition comprising a conjugate according to claim 10 and a pharmaceutically acceptable carrier.

15. The compound according to claim 2, wherein p is 1 and L is CH$_2$.

16. The compound according to claim 2, wherein Q is selected from the group consisting of —OR$^6$, —N(R$^6$)$_2$, —$^+$N(R$^6$)$_3$, —C(O)N(R$^6$)$_2$, —C(O)OR$^6$, —OC(O)R$^6$, —OC(O)OR$^6$, —OC(O)N(R$^6$)$_2$, —N(R$^6$)C(O)R$^6$, —N(R$^6$)C(O)OR$^6$ and —N(R$^6$)C(O)N(R$^6$)$_2$, wherein R$^6$ is independently selected from the group consisting of hydrogen, halogen, C$_1$-C$_{24}$ alkyl groups, C$_6$-C$_{24}$ (hetero)aryl groups, C$_2$-C$_{24}$ alkyl(hetero)aryl groups and C$_2$-C$_{24}$ (hetero)arylalkyl groups.

17. The compound according to claim 2, wherein Q is —OH.

18. The compound according to claim 2, wherein R$_1$ is hydrogen.

19. The compound according to claim 2, wherein R$^3$ is hydrogen or [(L)$_p$-Q].

20. The compound according to claim 18, wherein R$^3$ is hydrogen or [(L)$_p$-Q].

21. The compound according to claim 9, wherein R$^3$ is hydrogen.

22. The compound according to claim 9, wherein R$^3$ is [(L)$_p$-Q] and wherein p is 1, L is CH$_2$ and Q is OH.

23. The compound according to claim 21, wherein the compound is of the Formula (exo-IIa.2) or (endo-IIa.2):

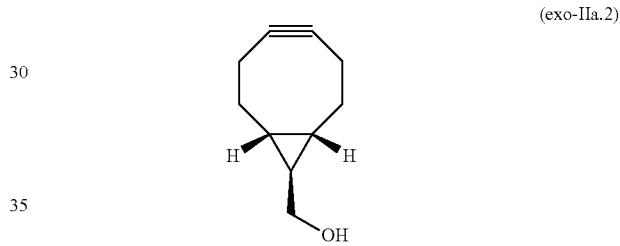

24. The compound according to claim 22, wherein the compound is of the Formula (IIa.7):

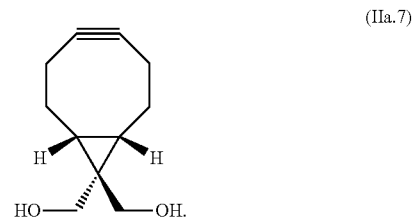

* * * * *